(12) United States Patent
Bulsara et al.

(10) Patent No.: US 10,821,057 B2
(45) Date of Patent: Nov. 3, 2020

(54) OCCLUSIVE COMPOSITIONS

(71) Applicant: LG HOUSEHOLD & HEALTH CARE LTD., Seoul (KR)

(72) Inventors: Pallav Arvind Bulsara, Warren, NJ (US); Martyn J. Clarke, Zebulon, NC (US); Anthony V. Rawlings, Cheshire (GB)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 15/770,873

(22) PCT Filed: Oct. 25, 2016

(86) PCT No.: PCT/US2016/058578
§ 371 (c)(1),
(2) Date: Apr. 25, 2018

(87) PCT Pub. No.: WO2017/074892
PCT Pub. Date: May 4, 2017

(65) Prior Publication Data
US 2018/0311121 A1    Nov. 1, 2018

Related U.S. Application Data

(60) Provisional application No. 62/247,773, filed on Oct. 29, 2015.

(51) Int. Cl.
| *A61K 8/06* | (2006.01) |
| *A61K 8/34* | (2006.01) |
| *A61K 8/55* | (2006.01) |
| *A61K 8/37* | (2006.01) |
| *A61K 8/36* | (2006.01) |
| *A61Q 19/00* | (2006.01) |
| *A61Q 17/00* | (2006.01) |
| *A61K 8/02* | (2006.01) |

(52) U.S. Cl.
CPC ............ *A61K 8/062* (2013.01); *A61K 8/0295* (2013.01); *A61K 8/342* (2013.01); *A61K 8/361* (2013.01); *A61K 8/37* (2013.01); *A61K 8/55* (2013.01); *A61K 8/553* (2013.01); *A61Q 17/00* (2013.01); *A61Q 19/00* (2013.01)

(58) Field of Classification Search
CPC ... A61K 8/06; A61K 8/34; A61K 8/55; A61K 8/37; A61K 8/36; A61Q 19/00; A61Q 17/00
See application file for complete search history.

(56) References Cited

U.S. PATENT DOCUMENTS

| 5,849,315 A | 12/1998 | Rerek et al. |
| 6,986,903 B2 | 1/2006 | Zulli et al. |
| 2006/0029657 A1 | 2/2006 | Popp et al. |
| 2007/0025951 A1* | 2/2007 | Foulger .................. A61K 8/92 424/74 |
| 2007/0027153 A1 | 2/2007 | Reeth et al. |
| 2009/0220616 A1 | 9/2009 | Joseph et al. |
| 2010/0048740 A1 | 2/2010 | Mercier et al. |
| 2012/0108661 A1 | 5/2012 | Orita et al. |
| 2013/0324499 A1 | 12/2013 | Pennick et al. |
| 2015/0272861 A1 | 10/2015 | Mazur et al. |

FOREIGN PATENT DOCUMENTS

| CN | 101360421 A | 10/2018 |
| EP | 2 670 376 A2 | 12/2013 |
| EP | 2 926 833 A1 | 10/2015 |
| WO | 2012/095393 A1 | 7/2012 |
| WO | 2012/152810 A1 | 11/2012 |
| WO | WO 2013/007599 A2 | 1/2013 |

OTHER PUBLICATIONS

Summers et al "The effect of lipids, with and without humectant, on skin xerosis," J Soc 1-3 Costmet Chem., 1996, vol. 47, pp. 27-39 Entire Document.
G. Pennick et al: "The effect of an amphiphilic self-assembled lipid lamellar phase on the relief of dry skin", International Journal of Cosmetic Science., vol. 34, No. 6, Sep. 1, 2012 (Sep. 1, 2012), pp. 567-574, XP055540514, NL ISSN: 0142-5463, DOI: 10.1111/j.1468-2494.2012.00749.x * table I ** p. 570, left-hand column* * p. 572 *.
EP Search Report dated Jun. 3, 2019.
U.S. Appl. No. 15/916,360.
U.S. Appl. No. 15/770,827.
U.S. Appl. No. 15/770,856.
Remco Hartkamp, et al.: "Composition Dependence of Water Permeation Across Multicomponent Gel-Phase Bilayers", J. Phys. Chem B. 2018, 122, 3113-3123.
Daniël Groen et al., "Is an orthorhombic lateral packing and a proper lamellar organization important for the skin barrier function?" Biochimica et Biophysica Acta, (2011) 1529-1537.
Bianca Perez et al: "Ultralong Fatty Acyl Derivatives as Occlusive Structure Lipids for Cosmetic Applications: Synthesis and Characterization", ACS Sustainable Chemistry & Engineering, vol. 4, No. 12; Sep. 26, 2016 (Sep. 26, 2016), pp. 7137-7146, XP055589871, ISSN: 2168-0485, DOI: 10.1021/acssuschemeng.6b02021.

(Continued)

*Primary Examiner* — Zohreh A Fay
(74) *Attorney, Agent, or Firm* — Vorys, Sater, Seymour & Pease LLP; Mih Suhn Koh

(57) ABSTRACT

The invention provides for a topical o/w emulsion having moisturizing, and protecting, repairing or restoring the skin lipid barrier of the lips of a mammal, and is a topical oil-in-water emulsion composition comprising: a discontinuous oil phase; a continuous aqueous phase comprising water; a thickening agent; at least one lamellar membrane structure comprising an alkyl amphiphilic component, an ester of a branched fatty acid and a branched fatty alcohol, a fatty acid, a fatty alcohol, and optionally a phospholipid; and wherein in use the composition has a water vapor transmission rate of less than 65 $g \cdot m^{-2} \cdot hr^{-1}$ measured in vitro.

12 Claims, 3 Drawing Sheets

(56) References Cited

OTHER PUBLICATIONS

Pennick, et al., "Superior effect of isostearyl isostearate on improvement in stratum corneum water permeability barrier function as examined by the plastic occlusion stress test." Int J Cosmet Sci, 32 (2010)304-312.

The Chinese Office Action—First Notification of Office Action, 14 pages with English Translation, dated Jul. 2, 2020.

* cited by examiner

OCCLUSIVE COMPOSITIONS

This application is a 371 of International Application No. PCT/US2016/058578, filed Oct. 25, 2016, which claims the benefit of U.S. Provisional Application No. 62/247,773, filed Oct. 29, 2015, which is incorporated herein in its entirety.

FIELD OF THE INVENTION

The present invention relates to novel occlusive compositions for topical application.

BACKGROUND OF THE INVENTION

WO 2012/104604 describes a blend for use in personal care compositions, which comprises at least one dialkyl amphiphilic component and at least one ester of a branched fatty acid and branched fatty alcohol. The blend may be used as the oil phase of an oil-in-water emulsion composition. The blend may further comprise a fatty acid and a fatty alcohol. Blends prepared in accordance with WO 2012/104604 are commercially available from Croda International PLC as DuraQuench™ blends. For example, DuraQuench™ IQ comprises potassium cetyl phosphate, isostearyl isostearate, behenic acid, cetyl alcohol and cetyl behenate. DuraQuench™ IQ SA comprises potassium cetyl phosphate, isostearyl isostearate, stearic acid, cetyl alcohol and cetyl stearate. The DuraQuench™ blends are adapted for use in personal care compositions and provide moisturization to the skin by forming a layer on the skin's surface and regulating water loss. See also Pennick et al., Intl J Cos Sci, 34, P 567-574 (2012).

However, there remains a need in the art for cosmetically elegant compositions which have improved levels of occlusivity as compared with those lipid mixtures described above and in those products commercially sold.

Accordingly, an object of the present invention is to provide a topical composition that minimizes trans-epidermal water loss (TEWL), e.g. reduces the amount/quantity of water that passes from inside the body though the epidermal layer (skin) to the surrounding atmosphere.

A further object of the present invention is to provide a topical composition which is convenient, easily applied to the skin and cosmetically elegant.

SUMMARY OF THE INVENTION

One embodiment of the disclosure is a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) at least one fatty alcohol; and optionally phosphatidyl choline;
wherein in use the composition has a water vapor transmission rate of less than 65 $g \cdot m^{-2} \cdot hr^{-1}$ measured in vitro using the modWVTR test methodology.

In one embodiment, the lamellar membrane blend has a molar % (also referred to herein as 'mol') of the alcohol or mixture of alcohols in the composition of from about 50 mol % to about 85 mol %. In another embodiment, the mol % is from about 60% to about 70%. In another embodiment, the mol % is from about 63 to about 69%.

In one embodiment, when the lamellar membrane blend comprises as the amphiphilic component, monoalkyl potassium cetyl phosphate, the molar % is from about 50 mol % to about 85 mol %. In another embodiment, the mol % is from about 50% to about 65%. In another embodiment, the mol % is from about 50 to about 62%.

In one embodiment, when the lamellar membrane blend comprises at least two fatty alcohols, the molar ratio of the second fatty alcohol in the composition to the amount of cetyl alcohol (from the Duraquench blend) is from about 4:1 to about 0.3:10. In another embodiment, the molar ratio of the second fatty alcohol in the composition to the amount of cetyl alcohol is from about 2:1 to about 0.5:1. In another embodiment, the molar ratio of the second fatty alcohol in the composition to the amount of cetyl alcohol is about 2.0:1.0. In another embodiment, the molar ratio of the second fatty alcohol in the composition to the amount of cetyl alcohol is about 1.25:1.

In an embodiment, the molar ratio of behenyl alcohol to cetyl alcohol is from about 0.3:1 to about 4:1. In another embodiment, the molar ratio is from about 0.34:1 to about 1.25:1.

In one embodiment, when the lamellar membrane blend comprises as the amphiphilic component, monoalkyl potassium cetyl phosphate, the molar ratio of the second fatty alcohol in the composition to the amount of cetyl alcohol is from about 1.0 to about 1.5:1. In one embodiment, the second fatty alcohol is behenyl alcohol.

In one embodiment, the lamellar membrane blend has a molar ratio of the fatty alcohol to the fatty acid of about 2.5:1 to about 19:1.0. In another embodiment, the molar ratio is about 3:1 to about 10:1. In another embodiment the mol ratio is about 5:1 to about 10:1. In yet another embodiment, the molar ratio is about 8:1 to about 9:1.

In one embodiment, when the lamellar membrane blend comprises as the amphiphilic component, monoalkyl potassium cetyl phosphate, the molar ratio of the fatty alcohol to the fatty acid of about 2.5:1 to about 15:1. In another embodiment, the molar ratio is from about 2.5:1 to about 6:1.

In one embodiment, the lamellar membrane blend has a molar % of fatty acid from about 4.5% to about 20%. In another embodiment, the molar % of the fatty acid is from about 7 to about 13%. In yet another embodiment, the molar % of the fatty acid is from about 7 to about 10%.

In one embodiment, when the lamellar membrane blend comprises as the amphiphilic component, monoalkyl potassium cetyl phosphate, the molar % of the fatty acid is from about 6% to about 20%. In another embodiment, the mol % of the fatty acid is from about 15 to about 20%. In yet another embodiment, the mol % of the fatty acid is from about 18 to about 20%.

In one embodiment, the lamellar membrane blend has a molar % of the phosphatidyl choline (PC), if present of 2.0 to about 8%. In another embodiment, the composition has a molar % of the phosphatidyl choline (PC), if present of about 7 to about 8%.

In one embodiment, when the lamellar membrane blend comprises as the amphiphilic component, monoalkyl potassium cetyl phosphate, the molar % of the phosphatidyl choline (PC), if present is from 6 to about 15.0%. In another embodiment, the molar % is from about 6 to about 9%. In yet another embodiment, the mol % is from about 6 to about 7%.

In one embodiment, the lamellar membrane blend has a molar ratio of the at least one fatty alcohol to the phosphatidyl choline of about 35:1 to about 6:1. In another embodiment, the molar ratio is about 20:1 to about 6:1. In another embodiment, the molar ratio is from about 10:1 to about 6:1. In yet another embodiment, the molar ratio is about 9:1 to about 8:1.

In one embodiment, when the lamellar membrane blend comprises as the amphiphilic component, monoalkyl potassium cetyl phosphate, the molar ratio of the at least one fatty alcohol to the phosphatidyl choline of about 20:1 to about 7:1. In another embodiment, the molar ratio is from about 9:1 to about 4.3 to 1.

In one embodiment, the lamellar membrane blend has a molar % of the ester from about 4.0% to about 18%. In another embodiment, the molar % is about 6 to about 9%. In another embodiment the molar % is about 7.5 to about 8.5%. In yet another embodiment the molar % is 8.0%.

In one embodiment, when the lamellar membrane blend comprises as the amphiphilic component, monoalkyl potassium cetyl phosphate, the molar % of the ester is from about 5.0% to about 18%. In one embodiment, the molar % is from about 7.5% to about 14%. In another embodiment, the mol % is from about 12.5 to about 14%.

In one embodiment, the lamellar membrane blend has a molar ratio of fatty alcohol to the ester of about 4.0:1 to about 19.0:1.0. In another embodiment, the mol ratio is about 7:1 to about 10:1. In another embodiment the mol % is about 7.5 to about 8.5:1.

In one embodiment, when the lamellar membrane blend comprises as the amphiphilic component, monoalkyl potassium cetyl phosphate, the molar ratio of the fatty alcohol to the ester is from about 3.4:1 to about 12:0:1 in another embodiment, the molar ratio is from about 3.44 to about 8. In another embodiment, the ratio is about 4.03:1.

In one embodiment, the lamellar membrane blend has a mol % of the alkyl amphiphilic component of about 2% to about 11%. In another embodiment, the mol % is about 4 to about 8%. In yet another embodiment, the mol % is about 6.0.

In one embodiment, when the lamellar membrane blend comprises an amphiphilic component which is monoalkyl potassium cetyl phosphate, the mol % is from about 4.5% to about 12.5%. In another embodiment, the mol % is about 4.5 to about 8%.

In one embodiment, the lamellar membrane blend has a molar ratio of fatty alcohol to the alkyl amphiphilic component of about 4:1 to about 25:1. In another embodiment, the mol ratio is about 9:1 to about 15:1. In yet another embodiment, the mol ratio is from about 10:1 to about 13:1.

In one embodiment, when the lamellar membrane blend comprises as the amphiphilic component, monoalkyl potassium cetyl phosphate, the molar ratio of the fatty alcohol to the monoalkyl amphiphilic component of about 4:1 to about 13:1. In another embodiment, the molar ratio is about 4:1 to about 6:1.

In one embodiment, the lamellar membrane blend has a molar % of about 2.0 to about 11 molar % alkyl amphiphilic component; a 5.0% to about 18% molar % of the ester; 6% to about 20 molar % of the fatty acid; and 50-85 molar % of the alcohol, and optionally 2.0 to about 8.0 molar % of the phosphatidyl choline.

In one embodiment, the lamellar membrane blend has a molar % of from about 4.5 to about 12 molar % of the monoalkyl amphiphilic component: from about 5 to about 18 mol % of the ester: about 6 to about 20 mol % of the fatty acid: about 50 to about 85 molar % of the fatty alcohol; and optionally about 6 to about 15 mol % of the phosphatidyl choline.

In another embodiment, the lamellar membrane blend has a molar % of from about 4.5 to about 12 mol % of the monoalkyl amphiphilic component: from about 7.5 to about 14 molar % of the ester: about 15 to about 20 molar % of the fatty acid: about 60 to about 70 molar % of the fatty alcohol; and optionally about 6 to about 9 molar % of the phosphatidyl choline.

Another embodiment of the disclosure is a method for moisturizing, and protecting, repairing, or restoring the skin lipid barrier of a mammal, the method comprising applying to the skin of the mammal in need thereof an effective amount of a topical oil-in-water emulsion composition comprising:
 (a) a discontinuous oil phase;
 (b) a continuous aqueous phase comprising water;
 (c) a thickening agent;
 (d) at least one lamellar membrane structure comprising
  (i) an alkyl amphiphilic component, (ii) an ester of a branched fatty acid and a branched fatty alcohol, (iii) a fatty acid, and (iv) a fatty alcohol; and
 wherein in use the composition has a water vapor transmission rate of less than 65 g·m$^{-2}$·hr$^{-1}$ measured in vitro using modWVTR test methodology.

Yet another embodiment of the disclosure is the use of a topical oil-in-water emulsion composition comprising:
 (a) a discontinuous oil phase;
 (b) a continuous aqueous phase comprising water;
 (c) a thickening agent;
 (d) at least one lamellar membrane structure comprising
  (i) an alkyl amphiphilic component, (ii) an ester of a branched fatty acid and a branched fatty alcohol, (iii) a fatty acid, and (iv) a fatty alcohol; and
 wherein in use the composition has a water vapor transmission rate of less than 65 g·m$^{-2}$·hr$^{-1}$ measured in vitro using modWVTR test methodology, for moisturizing, and protecting, repairing, or restoring the skin lipid barrier of a mammal.

A further embodiment of the disclosure is a topical oil-in-water emulsion composition comprising:
 (a) a discontinuous oil phase;
 (b) a continuous aqueous phase comprising water;
 (c) a thickening agent;
 (d) at least one lamellar membrane structure comprising
  (i) an alkyl amphiphilic component, (ii) an ester of a branched fatty acid and a branched fatty alcohol, (iii) a fatty acid, and (iv) a fatty alcohol; and
 wherein in use the composition has a water vapor transmission rate of less than 65 g·m$^{-2}$·hr$^{-1}$ measured in vitro using modWVTR test methodology, for use in moisturizing, and protecting, repairing, or restoring the skin lipid barrier of a mammal.

Yet a further embodiment of the disclosure is the use of a topical oil-in-water emulsion composition comprising:
 (a) a discontinuous oil phase;
 (b) a continuous aqueous phase comprising water;
 (c) a thickening agent;
 (d) at least one lamellar membrane structure comprising
  (i) an alkyl amphiphilic component, (ii) an ester of a branched fatty acid and a branched fatty alcohol, (iii) a fatty acid, and (iv) a fatty alcohol; and
 wherein in use the composition has a water vapor transmission rate of less than 65 g·m$^{-2}$·hr$^{-1}$ measured in vitro using modWVTR test methodology, in the manufacture of a cosmetic or pharmaceutical composition for moisturizing, and protecting, repairing, or restoring the skin lipid barrier of a mammal.

DETAILED DESCRIPTION OF THE INVENTION

Figure 1:
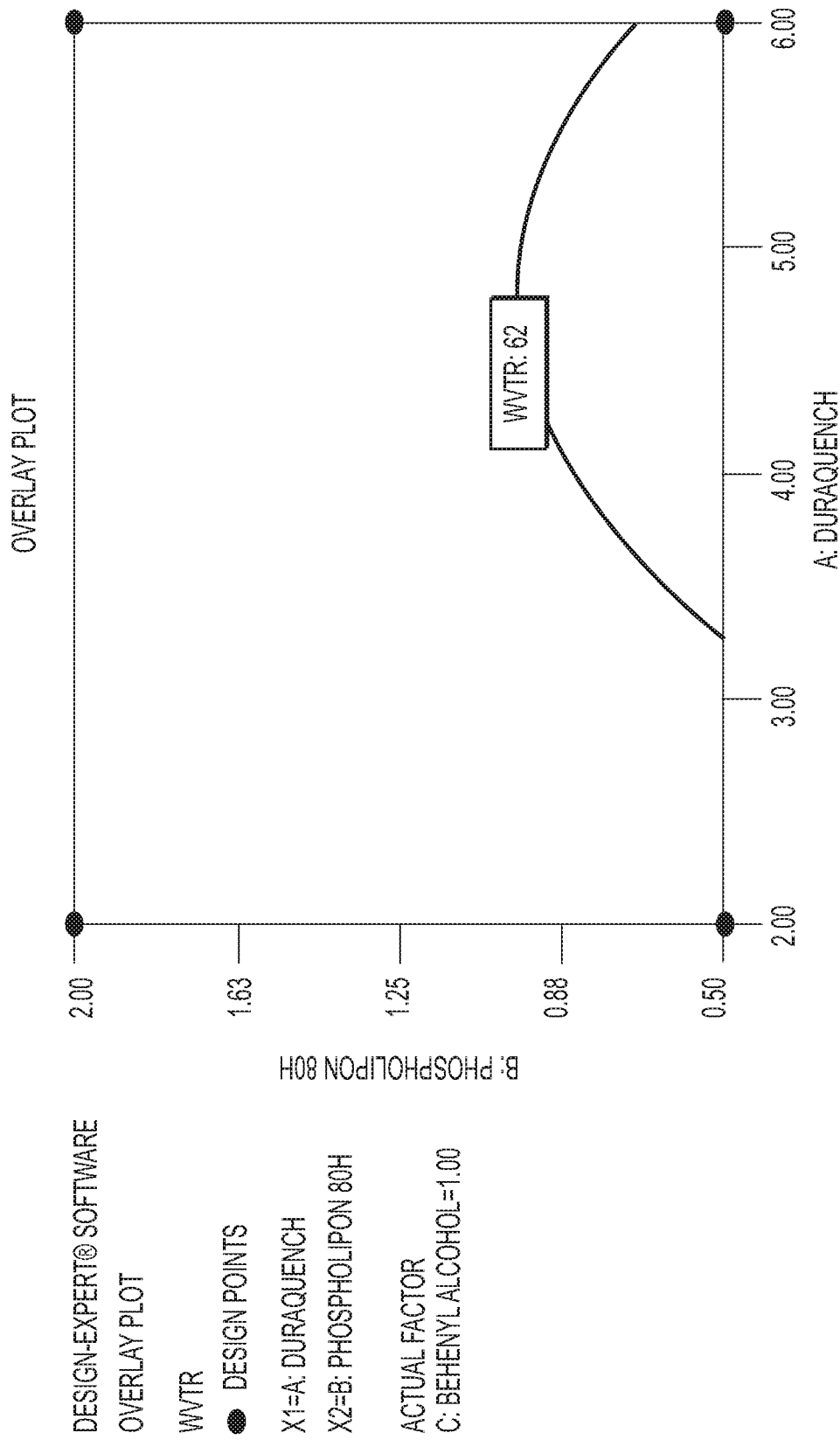
FIG. 1 illustrates the desirable region (light gray) where the water vapor transmission rate (WVTR) is less than 62 $g \cdot m^{-2} \cdot hr^{-1}$ for compositions containing 1% behenyl alcohol with varying levels of DuraQuench IQ and phospolipid.

In one embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol; and
wherein in use the composition has a water vapor transmission rate of less than 65 $g \cdot m^{-2} \cdot hr^{-1}$ measured in vitro using modWVTR test methodology.

The emulsion compositions of the present invention have improved levels of occlusivity compared with prior art compositions.

In one embodiment, the composition is a cream, lotion, balm, lip cream or stick lip balm. In an embodiment, the composition is a cream. In another embodiment, the composition is a lotion. In a further embodiment, the composition is a balm. In yet a further embodiment, the composition is a lip cream. In another embodiment, the composition is a stick lip balm.

The composition in use has a water vapor transmission rate (WVTR) of less than about 65 $g \cdot m^{-2} \cdot hr^{-1}$ measured in vitro. In a particular embodiment, the composition in use has a water vapor transmission rate of less than about 62 $g \cdot m^{-2} \cdot hr^{-1}$ measured in vitro. In another embodiment, the composition in use has a water vapor transmission rate of less than about 60 $g \cdot m^{-2} \cdot hr^{-1}$ measured in vitro.

In a further embodiment, the composition in use has a water vapor transmission rate from about 45 $g \cdot m^{-2} \cdot hr^{-1}$ to about 65 $g \cdot m^{-2} \cdot hr^{-1}$ measured in vitro. In another embodiment, the composition in use has a water vapor transmission rate from about 50 $g \cdot m^{-2} \cdot hr^{-1}$ to about 65 $g \cdot m^{-2} \cdot hr^{-1}$ measured in vitro. In another embodiment, the composition in use has a water vapor transmission rate from about 50 $g \cdot m^{-2} \cdot hr^{-1}$ to about 62 $g \cdot m^{-2} \cdot hr^{-1}$ measured in vitro. In an embodiment, the composition in use has a water vapor transmission rate from about 50 $g \cdot m^{-2} \cdot hr^{-1}$ to about 60 $g \cdot m^{-2} \cdot hr^{-1}$ measured in vitro using modWVTR test methodology In an embodiment, the composition in use has a water vapor transmission rate of about 50, 51, 52, 53, 54, 55, 56, 57, 58, 59, 60, 61, 62, 63, 64 or 65 $g \cdot m^{-2} \cdot hr^{-1}$ measured in vitro.

Oil Phase

The compositions of this disclosure comprise a discontinuous oil phase. The discontinuous oil phase is dispersed throughout the continuous aqueous phase.

In an embodiment, the discontinuous oil phase comprises at least one oil and/or fat. In one embodiment, the oil and/or fat is a mixture of two or more oils and/or fats.

Exemplary oils and fats include, but are not limited to, fatty acids, a source of fatty acids, fatty alcohols, esters, esters of glycerin (including mono-, di- and tri-esters), waxes, sterols, hydrocarbons, essential oils, vegetable oils and edible oils, silicone oils, and mixtures thereof.

In an embodiment, the at least one oil and/or fat is a fatty acid. In one embodiment, the fatty acid is a $C_{12}$ to $C_{36}$ fatty acid which may be saturated or unsaturated, branched or straight chained. In another embodiment, the fatty acid is a $C_{18}$ to $C_{36}$ fatty acid. In another embodiment, the fatty acid is a $C_{20}$ to $C_{26}$ fatty acid. In yet another embodiment, the fatty acid is a $C_{22}$ fatty acid.

Exemplary fatty acids include, but are not limited to, isostearic acid (also known as isoactadecanoic acid) (C18), linoleic acid (C18), linolenic acid (C18), oleic acid (C18), myristic acid (also known as tetradecanoic acid) (C14), ricinoleic acid (C18), columbinic acid (C18), arachidic acid (also known as eicosanoic acid) (C20), arachidonic acid (C20), heneicosic acid ($C_{21}$), erucic acid ($C_{22}$), lignoceric acid (also known as tetracosanoic acid) (C24), nervonic acid (C24), ceric acid ($C_{26}$), montanic acid ($C_{28}$), nonacosanoic acid ($C_{29}$), lacceric acid ($C_{32}$), geddic acid ($C_{34}$) and tetratriacontanol ($C_{36}$), eicosapentanoic acid (C20), palmitic acid (also known as hexadecanoic acid) (C16), stearic acid (also known as octadecanoic acid) (C18), behenic acid (also known as docosanoic acid)(C22), heptacosenoic acid (C27), nonacosanoic acid (C29), tricontanoic acid (C30), and mixtures thereof.

The fatty acid can be introduced into the present compositions from a variety of sources. In an embodiment, the fatty acid is provided in the composition as an oil or wax. Examples of oils or waxes useful in this regard include, but are not limited to, rice bran oil, rice bran wax, flaxseed oil, hempseed oil, pumpkin seed oil, canola oil, soybean oil, wheat germ oil, olive oil, grapeseed oil, borage oil, evening primrose oil, black currant seed oil, chestnut oil, corn oil, safflower oil, sunflower oil, sunflower seed oil, cottonseed oil, peanut oil, sesame oil and olus (vegetable) oil, and mixtures thereof.

In one embodiment, the source of fatty acids is shea butter, also known as Butyrospermum parkii, if chemically treated. Shea butter comprises five principal fatty acids, namely palmitic acid, stearic acid, oleic acid, linoleic acid and arachidic acid. Shea butter also comprises phytosterols.

In another embodiment, the at least one oil and/or fat is a fatty alcohol, which may be saturated or unsaturated. In one embodiment, the fatty alcohol is a branched or straight chain $C_{12}$-$C_{36}$ fatty alcohol. In one embodiment, the chain is branched. In another embodiment, the fatty alcohol is a branched or straight chain $C_{14}$-$C_{26}$ fatty alcohol. In another embodiment, the fatty alcohol is a branched or straight chain $C_{16}$ to $C_{22}$ fatty alcohol. In another embodiment, the fatty alcohol is a a branched or straight chain $C_{20}$-$C_{26}$ fatty alcohol. In another, the branched or straight chain is $C_{18}$-$C_{30}$ carbon atoms. In yet another embodiment, the branched or straight chain is $C_{20}$ to $C_{30}$ carbon atoms. In a further embodiment, the branched or straight chain is $C_{22}$ to $C_{28}$ carbon atoms. In another embodiment, the fatty alcohol is a $C_{18}$ or $C_{22}$ branched or straight chain fatty alcohol. In yet another embodiment, the fatty alcohol is a $C_{18}$ or $C_{22}$ branched fatty alcohol. In another embodiment, the fatty alcohol is a branched chain fatty alcohol. In another embodiment, the fatty alcohol is a straight chain fatty alcohol. In an embodiment, the fatty alcohol is a mixture of two or more fatty alcohols.

Exemplary straight chain fatty alcohols for use in the invention include, but are not limited to, decyl alcohol ($C_{10}$), lauryl alcohol ($C_{12}$), tridecyl alcohol ($C_{13}$), myristyl alcohol ($C_{14}$), pentadecyl alcohol ($C_{15}$), cetyl alcohol ($C_{16}$), cetearyl alcohol ($C_{16}/C_{18}$), palmitoleyl alcohol ($C_{16}$), heptadecyl alcohol ($C_{17}$), stearyl alcohol ($C_{18}$), nonadecyl alcohol ($C_{19}$), arachidyl alcohol ($C_{20}$), heneicosyl alcohol ($C_{21}$), behenyl alcohol ($C_{22}$), erucyl alcohol ($C_{22}$), lignoceryl alcohol ($C_{24}$), ceryl alcohol ($C_{26}$), 1-heptacosanol ($C_{27}$), montanyl alcohol ($C_{28}$), 1-nonacosanol ($C_{29}$), myricyl alcohol ($C_{30}$), lacceryl alcohol ($C_{32}$), geddyl alcohol ($C_{34}$) and tetratriacontanol ($C_{36}$), and mixtures thereof.

In one embodiment, the fatty alcohols include, but are not limited to, behenyl alcohol, isostearyl alcohol, caprylyl alcohol, decyl alcohol, lauryl alcohol, myristyl alcohol, lanolin alcohol, arachidyl alcohol, oleyl alcohol, palm alcohol, isocetyl alcohol, cetyl alcohol, stearyl alcohol and cetearyl alcohol, and mixtures thereof.

In yet another embodiment, the at least one oil and/or fat is an ester. Exemplary esters include, but are not limited to, coco-caprylate/caprate, diethyl sebacate, diisopropyl adipate, diisopropyl dilinoleate, ethyl oleate, ethylhexyl hydroxystearate, glycol distearate, glycol stearate, hydroxyoctacosanyl hydroxystearate, isopropyl isostearate, isostearyl isostearate, isopropyl myristate, isopropyl palmitate, isopropyl stearate, methyl glucose sesquistearate, methyl laurate, methyl salicylate, methyl stearate, myristyl lactate, octyl salicylate, oleyl oleate, PPG-20 methyl glucose ether distearate, propylene glycol diacetate, propylene glycol dicaprylate, propylene glycol monolaurate, propylene glycol monopalmitostearate, propylene glycol ricinoleate and sucrose distearate, and mixtures thereof.

In a further embodiment, the at least one oil and/or fat is an ester of glycerin. Exemplary esters of glycerin include, but are not limited to, caprylic/capric triglycerides, caprylic/capric/succinic triglyceride, cocoglycerides, glyceryl citrate, glyceryl isostearate, glyceryl laurate, glyceryl monostearate, glyceryl oleate, glyceryl palmitate, glyceryl ricinoleate, glyceryl stearate, mono and diglyceride, PEG-12 glyceryl laurate, PEG-120 glyceryl stearate, polyglyceryl-3 oleate, polyoxyl glyceryl stearate, tallow glycerides and medium chain triglycerides, and mixtures thereof. In one particular embodiment, the ester of glycerin is caprylic/capric triglyceride. In one embodiment, the source of ester of glycerin is shea butter, also known as Butyrospermum parkii. In another embodiment, the ester of glycerin is caprylic/capric triglycerides, alone or in combo with shea butter.

In yet a further embodiment, the at least one oil and/or fat is a wax. Exemplary waxes include, but are not limited to, animal waxes, plant waxes, mineral waxes, silicone waxes, synthetic waxes and petroleum waxes. Suitable waxes include, but are not limited to, rice bran wax, carnauba wax, paraffin wax, white wax, candelilla wax, beeswax, jojoba wax, ozokerite and a spingolipid or a spingolipid mimic such as a ceramide, and mixtures thereof.

In an embodiment, the at least one oil and/or fat is wax is a sphingolipid or a sphingolipid mimic. Ceramides are a family of lipid molecules composed of sphingosine and a fatty acid. They contain an acyl linkage, and most abundant chain length in healthy skin is $C_{24}$-$C_{26}$ with a small fraction having an acyl chain length of $C_{16}$-$C_{18}$. Ceramides are found extensively in the stratum corneum. Ceramides are commercially available from major chemical suppliers such as Evonik, Mobile, Ala., USA or Sigma Chemical Company, St. Louis, Mo., U.S.A.

Exemplary ceramides useful in the present compositions include, but are not limited to, ceramide-1, -2, -3, -4, -5, -6 or -7, and mixtures thereof. Other ceramides known to those of skill in the art as useful in topical compositions are further contemplated as useful in the present compositions. In one embodiment, the ceramide is ceramide-3.

In an embodiment, the at least one oil and/or fat is a sterol. Exemplary sterols include, but are not limited to, *Brassica Campestris* sterols, $C_{10}$-$C_{30}$ cholesterol/lanosterol esters, canola sterols, cholesterol, cholesterols, *glycine soja* sterols, PEG-20 phytosterol and phytosterols, and mixtures thereof.

The term "phytosterol" refers to plant sterols and plant stanols. Plant sterols are naturally occurring cholesterol-like molecules found in all plants, with the highest concentrations occurring in vegetable oils. Plant stanols are hydrogenation compounds of the respective plant sterols.

Phytosterols are natural components of common vegetable oils. Exemplary sources of phytosterols useful in this regard include, but are not limited to, shea butter, vegetable oil, tall oil, sesame oil, sunflower oil, sunflower seed oil, rice bran oil, cranberry seed oil, pumpkin seed oil and avocado wax, and mixtures thereof. In one particular embodiment, the source of phytosterols is shea butter.

Phytosterols are typically incorporated in the basal membrane of the skin and can pass to the skin's surface through the differentiation of skin cells. Accordingly, phytosterols provide an improved caring and protecting effect. The topical application of phytosterols also usually leads to an increased skin moisture level and to increased lipid content. This improves the desquamation behavior of the skin and reduces erythemas which may be present. R. Wachter, Parf. Kosm., Vol. 75, p. 755 (1994) and R. Wachter, Cosm. Toil., Vol. 110, p. 72 (1995), each of which are incorporated herein by reference in their entirety, further demonstrate these advantageous properties of phytosterols.

In another embodiment, the at least one oil and/or fat is a hydrocarbon. Exemplary hydrocarbons include, but are not limited to, dodecane, petrolatum, mineral oil, squalane, squalene and paraffin, and mixtures thereof. In one embodiment, the hydrocarbon is petrolatum or a mixture of petrolatum and another oil or fat. In another embodiment, the hydrocarbon is a mixture of petrolatum and a second hydrocarbon. In another embodiment, the hydrocarbon is a mixture of mineral oil and a second hydrocarbon. In yet another embodiment, the hydrocarbon is a mixture of petrolatum and squalane. In yet another embodiment, the hydrocarbon is a mixture of mineral oil and squalane. In yet another embodiment, the hydrocarbon is a mixture of petrolatum and mineral oil.

In an embodiment, the hydrocarbon is squalane. Squalane helps enhance the skin's natural barrier function, protect the skin against the elements, and boost the skin's ability to retain moisture. Squalane is a component of human stratum corneum. Squalane is available in purified form (see e.g. Fitoderm® available from BASF) and may be used in the compositions in its purified form. Alternatively, an oil which is rich in squalane may be used.

Exemplary sources of squalane useful in the present compositions include, but are not limited to, shark liver oil, olive oil, palm oil, wheat germ oil, amaranth oil, rice bran oil and sugar cane.

In yet another embodiment, the at least one oil and/or fat is an essential oil. Exemplary essential oils include, but are not limited to, primrose oil, rose oil, *eucalyptus* oil, borage oil, bergamot oil, chamomile oil, citronella oil, lavender oil, peppermint oil, pine oil, pine needle oil, spearmint oil, tea tree oil and wintergreen oil, and mixtures thereof.

In a further embodiment, the at least one oil and/or fat is a vegetable oil. Exemplary vegetable oils include, but are not limited to, olus (vegetable) oil, almond oil, aniseed oil, canola oil, castor oil, coconut oil, corn oil, avocado oil, cottonseed oil, olive oil, palm kernel oil, peanut oil, sunflower oil, safflower oil and soybean oil, and mixtures thereof, including all hydrogenated forms of these oils as well. One embodiment is the use of olive oil and/or vegetable oil.

In yet a further embodiment, the at least one oil and/or fat is an edible oil. Exemplary edible oils include, but are not limited to, cinnamon oil, clove oil, lemon oil and peppermint oil, and mixtures thereof.

In one embodiment, the oil and/or fat is a fatty acid, a source of fatty acids, or an ester of glycerin as described herein.

Advantageously, many of the oils and/or fats used in embodiments of the present invention are the same or similar to the lipids found in human stratum corneum.

Suitably, the discontinuous oil phase is present in an amount from about 5% to about 75% by weight, based on the total weight of the composition. In an embodiment, the discontinuous oil phase is present in an amount from about 5% to about 50% by weight, based on the total weight of the composition. In another embodiment, the discontinuous oil phase is present in an amount from about 5% to about 45% by weight, based on the total weight of the composition. In yet another embodiment, the discontinuous oil phase is present in an amount from about 5% to about 25% by weight, based on the total weight of the composition.

Aqueous Phase

The compositions of the invention comprise a continuous aqueous phase. The aqueous phase comprises water. Suitably, any additional components which are water miscible will be dissolved in this aqueous phase.

Suitably, the continuous aqueous phase is present in an amount from about 25% to about 90% by weight, based on the total weight of the composition. In another embodiment, the continuous aqueous phase is present in an amount from about 45% to about 90% by weight, based on the total weight of the composition. In yet another embodiment, the continuous aqueous phase is present in an amount from about 50% to about 90% by weight, based on the total weight of the composition. In a further embodiment, the continuous aqueous phase is present in an amount from about 60% to about 90% by weight, based on the total weight of the composition.

In an embodiment, the continuous aqueous phase comprises water in an amount from about 10% to about 90% by weight, in an amount from about 10% to about 60% by weight, in another embodiment from about 10% to about 40% by weight, and in another embodiment from about 10% to about 35% by weight, based on the total weight of the composition.

In an embodiment, the continuous aqueous phase comprises water in an amount from about 50% to about 90% by weight, based on the total weight of the composition. In another embodiment, the continuous aqueous phase comprises water in an amount from about 55% to about 85% by weight, based on the total weight of the composition.

In an embodiment, the continuous aqueous phase comprises glycerin in an amount from about 1% to about 40% by weight, based on the total weight of the composition. In another embodiment, the continuous aqueous phase comprises glycerin in an amount from about 5% to about 15% by weight, based on the total weight of the composition. In an embodiment, the continuous aqueous phase comprises glycerin in an amount of about 10% by weight, based on the total weight of the composition.

In another embodiment, the glycerin in the aqueous phase is present in an amount from about 12% to about 40% by weight, based on the total weight of the composition. In yet another embodiment, the glycerin in the aqueous phase is present in an amount from about 20% to about 30% by weight, based on the total weight of the composition. In yet another embodiment, the glycerin in the aqueous phase is present in an amount from about 20% to about 25% by weight, based on the total weight of the composition.

In one embodiment, the continuous aqueous phase may also include a sugar alcohol, such as glucose, glycerol, sorbitol, mannitol, maltitol, galactitol, erythritol, xylitol, inositol, lactitol, and mixtures thereof. In one embodiment, the sugar alcohol is glucose. The sugar alcohol may be present in an amount from about 1% to about 20% by weight, based on the total weight of the composition. In an embodiment, the amount of sugar alcohol is from about 10% to about 15% by weight, based on the total weight of the composition. In another embodiment, the amount of sugar alcohol is about 10%, 11%, 12%, 13%, 14% or 15% by weight, based on the total weight of the composition.

The continuous aqueous phase may further comprise other water miscible components, such as for example, water miscible thickening agents, humectants and pH adjusting agents.

Thickening Agent

The compositions of the invention comprise a thickening agent or rheology modifier. In an embodiment, the thickening agent is a mixture of two or more thickening agents.

The function of the thickening agent is to stabilize the discontinuous oil phase of the composition. The thickening agent may also provide hardness and structural support useful in forming a stick composition, for example. Thickening agents may be water miscible which are used to thicken the aqueous portion of the emulsion composition. Other thickening agents are nonaqueous making them suitable for thickening the oil phase of the emulsion composition. Yet other thickening agents act at the oil-water interface.

Exemplary water miscible thickening agents include, but are not limited to, a cellulose derivative such as carboxymethylcellulose, hydroxyethylcellulose, hydroxypropylcellulose, hydroxypropyl methylcellulose; agar; carrageenan; curdlan; gelatin; gellan; β-glucan; tragacanth gum; guar gum; gum arabic; locust bean gum; pectin; starch; a carbomer, such as sodium carbomer; a xanthan derivative such as dehydroxanthan gum and xanthan gum; salts thereof, or a combination or mixture thereof.

Exemplary nonaqueous thickening agents include, but are not limited to, acrylate copolymers, VP/Eicosene copolymer, waxes, fatty alcohols and fatty acids, as described herein.

In an embodiment, the thickening agent is an acrylate copolymer, such as acrylates/C10-30 alkyl acrylate cross polymer, polyacrylate crosspolymer-6, or a mixture of hydroxyethyl acrylate and sodium acryloyldimethyl taurate copolymer.

In one embodiment, the thickening agent is xanthan gum. In another embodiment, the thickening agent is dehydroxanthan gum. In yet another embodiment, the thickening agent is a carbomer or a salt thereof, such as sodium carbomer. In a further embodiment, the thickening agent is hydroxyethylcellulose.

In one embodiment, the thickening agent is a fatty alcohol. Suitable fatty alcohols include, but are not limited to, behenyl alcohol, isostearyl alcohol, caprylyl alcohol, decyl alcohol, lauryl alcohol, myristyl alcohol, lanolin alcohol, arachidyl alcohol, oleyl alcohol, palm alcohol, isocetyl alcohol, cetyl alcohol, stearyl alcohol and cetearyl alcohol, and mixtures thereof.

Other suitable fatty alcohols include, but are not limited to, tridecyl alcohol, pentadecyl alcohol, isocetyl alcohol, palmitoleyl alcohol, heptadecyl alcohol, isostearyl alcohol, oleyl alcohol, nonadecyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, lacceryl alcohol, geddyl alcohol, tetratriacontanol, and lanolin alcohol, and mixtures thereof.

In one embodiment, the thickening agent is a fatty acid (which may be saturated or unsaturated, branched or straight chained), or a source of fatty acids, and mixtures thereof.

Suitable fatty acids include, but are not limited to, isostearic acid, linoleic acid, linolenic acid, oleic acid, myristic acid, ricinoleic acid, columbinic acid, arachidic acid, arachidonic acid, lignoceric acid, nervonic acid, eicosapentanoic acid, palmitic acid, stearic acid and behenic acid, and mixtures thereof.

Other exemplary fatty acids include, but are not limited to lauric acid, tridecylic acid, myristic acid, pentadecylic acid, margaric acid, oleic acid, nonadecylic acid, arachidic acid, arachidonic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid and hexatriacontylic acid, and mixtures thereof.

In one embodiment, the thickening agent comprises a mixture of fatty alcohols, a cellulose derivative, a xanthan derivative, a non-aqueous agent, and a carbomer. In one embodiment, the thickening agent comprises behenyl alcohol, dehydroxanthan gum, VP/Eicosene copolymer, acrylates/C10-30 alkyl acrylate cross polymer and sodium carbomer.

In an embodiment, the thickening agent is a mixture of polyacrylate crosspolymer-6 and hydroxyethyl acrylate/sodium acryloyldimethyl taurate copolymer.

Suitably, the thickening agent is present in an amount from about 0.5% to about 10% by weight, based on the total weight of the composition. In an embodiment, the thickening agent is present in an amount from about 0.5% to about 5% by weight, based on the total weight of the composition.

Lamellar Membrane Structure

The compositions of the invention comprise at least one lamellar membrane structure. Generally this refers to a planar lipid bilayer sheet, or a slight curve around a droplet of oil. They may also exist as separate discrete lamellae in the bulk aqueous phase. This is in contrast to a rounded formed liposomal structure. In another embodiment, the respective lamellar membrane structures form two or more stacked lamellar membrane structures, sometimes referenced as a liquid crystal. Two lamellar membrane structures stacked together, one on top of the other, is known as a double lamellar membrane structure.

Figure 3:
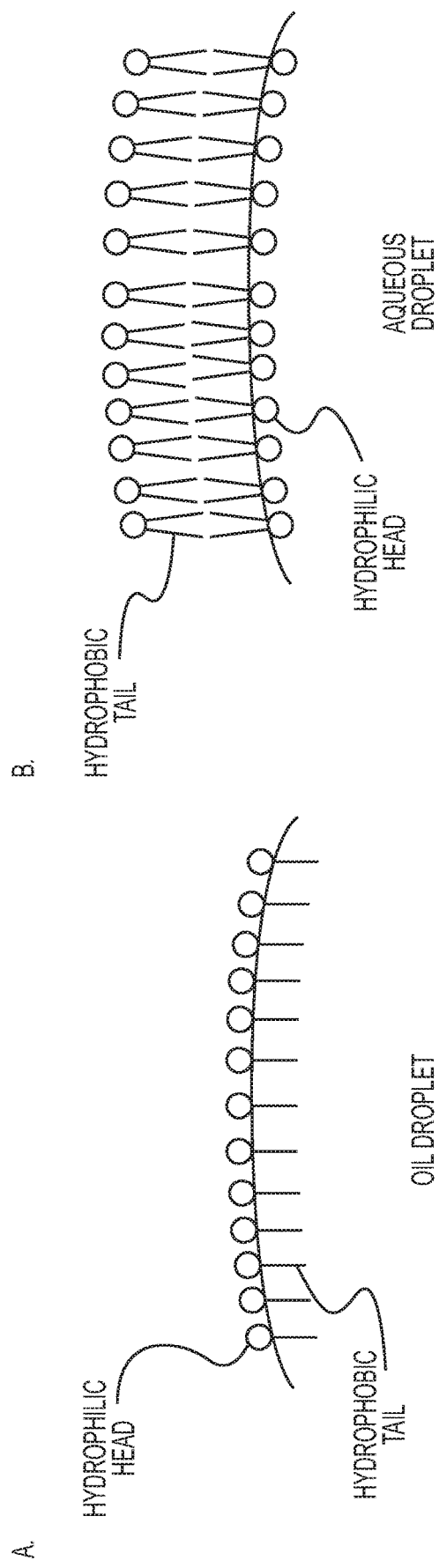
FIG. 3 illustrates key physical differences between an oil in water emulsion that can form a lamellar structure (A) and a liposome (B).

FIG. 3 illustrates the key physical difference between an oil in water emulsion that can form a lamellar structure (A) and a liposome (B). In an O/W emulsion the surfactant-emulsifiers orientate so that the hydrophilic heads face out into the continuous phase and the hydrophobic tails are anchored within the oil droplet. In the case of a liposome, these are typically aqueous filled cores where the hydrophilic heads of the interfacial layer of surfactant-emulsifer (here shown as a dialkyl phospholipid which can form liposomal structures) orientated toward the hydrophilic aqueous core and for the outermost layer, orientated towards the continuous phase.

Even if systems contain lamellar forming ingredients such as those further described herein, those systems can be prepared in a manner that will yield either a liposome or O/W emulsion. The physical characteristics of each system is different and is outlined below.

| Property | O/W Emulsion | Aqueous Core Liposome |
| --- | --- | --- |
| Droplet size | Typically >1000 nm | Range from 25 nm to 500 nm |
| Opacity | Very often white in appearance due to greater interaction with visible light. | Can be translucent to blue due to wavelength of light absorption/reflection |
| Rheology/Viscosity | Mid to high viscosity system (attributable to long range interactions between droplets) | Tend towards low viscosity systems (limited long range interactions between systems) |
| Dynamic Lamellar Structure (Viscosity Building) | Viscosity can build post manufacture due to thermodynamic equilibration. Lamellar structure builds with time causing an increase in viscosity. | Viscosity is relatively stable as lamellar structure has been established during the manufacturing process. |

The properties described above are measurable using standard lab measurement methods available in the art. All of these properties will clearly provide for an accurate designation of those O/W emulsions (microscopy, rheology, visual assessment) having lamellar structures (e.g. with FTIR/XRD).

According to the invention, the at least one lamellar membrane structure comprises (i) an alkyl amphiphilic component, (ii) an ester of a branched fatty acid and a branched fatty alcohol, (iii) a fatty acid, and (iv) a fatty alcohol. The at least one lamellar membrane structure optionally comprises a phospholipid.

Another embodiment is a topical oil-in-water emulsion composition comprising:
(a) a discontinuous oil phase;
(b) a continuous aqueous phase comprising water;

(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol; (v) a second long chain fatty alcohol; and (v) optionally a phospholipid;
wherein in use the composition has a water vapor transmission rate of less than 65 g·m$^{-2}$·hr$^{-1}$ measured in vitro using modWVTR test methodology.

In one embodiment the lamellar blend contains a fatty alcohol of C16-18 chain length (branched or straight chain), and a second longer (branched or straight chain) fatty alcohol of a C22-C30 carbon atoms.

Suitably, the components of the lamellar membrane structure, known as the "lamellar membrane blend", are present in an amount from about 2% to about 20% by weight, based on the total weight of the composition. In an embodiment, the lamellar membrane blend is present in an amount from about 2% to about 15% by weight, based on the total weight of the composition. In another embodiment, the lamellar membrane blend is present in an amount of about 2%, 3%, 4%, 5%, 6%, 7%, 8%, 9%, 10%, 11%, 12%, 13%, 14% or 15% by weight, based on the total weight of the composition.

As used herein the term "long chain" or "fatty" such as used in reference to "fatty alcohol" or "fatty acid", etc. refers to a hydrocarbon backbone chain which may be straight or branched, saturated or unsaturated, and is suitably composed of 12 to 36 carbon atoms. In one embodiment, the chain is 16 to 26 carbon atoms. In another embodiment the chain is 16 to 22 carbon atoms. In one embodiment, the chain is 22 to 30 carbon atoms. In one embodiment, the chain is 16 to 26 carbon atoms. In another embodiment the chain is 16 to 22 carbon atoms. In another embodiment, the chain is 20 to 22 carbon atoms. In another embodiment, the chain is from 20 to 30 carbon atoms, suitably 22 to 30 carbon atoms. In another embodiment the chain is from 22 to 28 carbon atoms.

Suitably, the components of the lamellar membrane structure, taken together, have a critical packing parameter (CPP) from about 0.9 to about 1.

The CPP is calculated according to the formula:

$$CPP = v/al,$$

in which v is the real volume of the hydrophobic chain(s), a is the cross-sectional area of the hydrophilic head group(s), and l is the approximate length of the hydrophobic chain(s). The CPP is described in more detail in S. Friberg, J. Soc. Cosmet. Chem., 1990, 41, 155-171, the contents of which is hereby incorporated by reference.

Alkyl Amphiphilic Component

The alkyl amphiphilic component may be a dialkyl amphiphilic component and/or a monoalkyl amphiphilic component.

The term "dialkyl amphiphilic component" as used herein refers to a component having both hydrophilic and lipophilic properties. In an embodiment, the dialkyl amphiphilic component comprises a large hydrophilic head group and a long hydrophobic tail comprising two alkyl groups. In an embodiment, the two alkyl groups are long chain alkyl groups.

The dialkyl amphiphilic component may be ionic (i.e. anionic, cationic, or zwitterionic) or non-ionic.

When the dialkyl amphiphilic component is anionic, the anionic functionality can be provided by, for example, a phosphorus acid group or salt thereof or a sulphur acid group or salt thereof. Suitable phosphorus acid groups include —OP(=O)(OH)O—, —(OA)$_n$OP(=O)(OH)O—, and —(OA)$_n$OP(=O)(OH)O(AO)$_m$—, where A represents an alkylene group, for example ethylene, propylene, and so on, and m and n are from 1 to 60, desirably 5 to 30. Suitable sulphur acid groups include sulphosuccinate: —OC(O)CH(SO$_3$H)CH$_2$C(O)O—, and alkoxylated sulphosuccinates: —(OA)$_n$OC(O)CHOSO$_3$H)CH$_2$C(O)O—, and —(OA)$_n$OC(O)CH((SO$_3$H)CH$_2$C(O)O(AO)$_m$—, where A, n and m are as defined above.

When the dialkyl amphiphilic component is cationic, the cationic functionality may be provided by, for example, dialkyl dimethyl amines: —N$^+$(CH$_3$)$_2$—, or imidazolines.

When the dialkyl amphiphilic component is nonionic, the nonionic hydrophilic functionality may be provided by, for example, esters of sorbitol, sorbitan, sucrose and polyglycerol, and alkoxylates thereof.

In an embodiment, the dialkyl amphiphilic component is ionic. In another embodiment, the dialkyl amphiphilic component is anionic. In an embodiment, the anionic functionality is provided by a phosphorus acid group or a salt thereof. In another embodiment, the anionic functionality is provided by a phosphate group.

In one embodiment, the dialkyl amphiphilic component is a salt. In another embodiment, the salt forming moiety is an alkali metal, particularly lithium, sodium or potassium, ammonium, including amine or hydroxyl-substituted amine, e.g. alkanoamine, onium, or amine, particularly alkylamine, especially tertiary alkylamine and hydroxy-substituted amine, e.g. alkanoamine, especially tertiary alkanoamine such as triethanolamine. Salts can generally be made from free acid precursors by direct reaction with an appropriate base. Desirably, the salt forming moiety is an alkali metal, preferably sodium or potassium, most preferably potassium.

The dialkyl functionality of the amphiphilic component may be provided by any two suitable alkyl groups. In an embodiment, the alkyl groups are long chain alkyl groups. The alkyl groups may be the same or different. In an embodiment, the alkyl groups are the same as each other.

Each alkyl group may be independently selected from the group including linear and branched alkyl groups. As used herein, the term alkyl refers to any saturated hydrocarbyl group which is a monovalent radical having the general formula C$_n$H$_{2n+1}$. The alkyl groups may each independently contain one or more unsaturated bonds, i.e. one or more double C=C bonds. In an embodiment, each alkyl group is independently selected from the group consisting of C10 to C30 alkyl groups. In another embodiment, each alkyl group is independently selected from the group consisting of C12 to C26 alkyl groups. In yet another embodiment, each alkyl group is independently selected from the group consisting of C14 to C22 alkyl groups. In one embodiment, the alkyl groups are C16 alkyl groups.

In an embodiment, the dialkyl amphiphilic component is present in combination with a monoalkyl amphiphilic component. When present, the monoalkyl amphiphilic component is a monoalkyl equivalent of the dialkyl amphiphilic component, i.e. the monoalkyl amphiphilic component is the same as the dialkyl amphiphilic component with one alkyl group substituted by H or a short chain alkyl group, for example, a methyl, ethyl or propyl group.

In one embodiment, the dialkyl amphiphilic component is potassium dicetyl phosphate.

In another embodiment, the monoalkyl amphiphilic component is potassium monocetyl phosphate.

In yet another embodiment, the lamellar membrane blend comprises a combination of potassium dicetyl phosphate and potassium monocetyl phosphate.

The term "monoalkyl amphiphilic component" as used herein refers to a component having both hydrophilic and lipophilic properties. In an embodiment, the monoalkyl amphiphilic component comprises a large hydrophilic head group and a long hydrophobic tail comprising an alkyl group. In an embodiment, the alkyl group is a long chain alkyl group.

The monoalkyl amphiphilic component may be ionic (i.e. anionic or cationic) or non-ionic. When the monoalkyl amphiphilic component is anionic, the anionic functionality can be provided by, for example, a phosphorus acid group or salt thereof or a sulphur acid group or salt thereof, as described herein for the dialkyl amphiphilic component.

When the monoalkyl amphiphilic component is cationic, the cationic functionality may be provided by, for example, an alkyl dimethyl amine: —$N^+(CH_3)_2$—, or imidazolines, as described herein for the dialkyl amphiphilic component.

When the monoalkyl amphiphilic component is nonionic, the nonionic hydrophilic functionality may be provided by, for example, esters of sorbitol, sorbitan, sucrose and polyglycerol, and alkoxylates thereof, as described herein for the dialkyl amphiphilic component.

In an embodiment, the monoalkyl amphiphilic component is ionic. In another embodiment, the monoalkyl amphiphilic component is anionic. In an embodiment, the anionic functionality is provided by a phosphorus acid group or a salt thereof. In another embodiment, the anionic functionality is provided by a phosphate group.

In one embodiment, the monoalkyl amphiphilic component is a salt, as described herein for the dialkyl amphiphilic component.

The alkyl functionality of the monoalkyl amphiphilic component may be provided by any suitable alkyl group. In an embodiment, the alkyl group is a long chain alkyl group. Mixtures of monoalkyl amphiphilic components may be used where their alkyl group may be the same or different. In an embodiment, the alkyl groups are the same as each other.

As used herein, the term "alkyl" in the monoalkyl amphiphilic component refers to any saturated hydrocarbyl group which is a monovalent radical having the general formula $C_nH_{2n+1}$. The alkyl group may contain one or more unsaturated bonds, i.e. one or more double C=C bonds. In an embodiment, the alkyl group is selected from the group consisting of a C10 to C30 alkyl group. In another embodiment, the alkyl group is selected from the group consisting of a C12 to C26 alkyl group. In yet another embodiment, the alkyl group is selected from the group consisting of a C14 to C22 alkyl group. In one embodiment, the alkyl group is a C16 alkyl.

In an embodiment, the alkyl amphiphilic component is potassium monocetyl phosphate.

In an embodiment, the alkyl amphiphilic component is present in an amount from about 1% to about 75% by weight, based on the total weight of the lamellar membrane blend. In another embodiment, the alkyl amphiphilic component is present in an amount from about 5% to about 50% by weight, based on the total weight of the lamellar membrane blend. In yet another embodiment, the alkyl amphiphilic component is present in an amount from about 10% to about 35% by weight, based on the total weight of the lamellar membrane blend. In a further embodiment, the alkyl amphiphilic component is present in an amount from about 15% to about 25% by weight, based on the total weight of the lamellar membrane blend.

In an embodiment, the alkyl amphiphilic component is present in an amount from about 1% to about 20% by weight, based on the total weight of the lamellar membrane blend. In another embodiment, the alkyl amphiphilic component is present in an amount from about 1% to about 15% by weight, based on the total weight of the lamellar membrane blend.

Ester of a Branched Fatty Acid and a Branched Fatty Alcohol

In an embodiment, the ester is formed from a branched or straight chain fatty acid and a branched or straight chain fatty alcohol comprising a mixture of compounds having mono- and poly-branching in the acid and alcohol originating parts of the ester. In one embodiment, the fatty acid and fatty alcohol are alkyl branched. In an embodiment, when the composition comprises an ester of a branched or straight chain fatty acid and a branched or straight chain fatty alcohol, the composition may further comprise a fatty acid.

It is recognized that because there are two components to the ester, either one or both of them can be branched or straight chained components, e.g. the ester can be mixed. For example, the fatty acid component may be branched and the fatty alcohol may be straight chained. Alternatively, the fatty acid component may be straight chained and the fatty alcohol may be branched. In another embodiment, both the acid and the alcohol may be branched. In yet another embodiment both the acid and the alcohol may be straight chained.

In one embodiment, the branched fatty acid component of the ester is a $C_{12}$ to $C_{36}$ branched fatty acid, a C12 to C30 branched fatty acid, a $C_{14}$ to $C_{26}$ branched fatty acid, a C16 to C22 branched fatty acid, or a C18 branched fatty acid. In one embodiment, the branched fatty acid component of the ester is a C18 branched fatty acid.

Fatty acids suitable for use herein can be obtained from natural sources. For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures may be used.

The fatty acid component of the ester may comprise a mixture of branched and linear fatty acids. Preferably, the fatty acid mixture comprises greater than about 70%, more preferably from about 73% to about 95%, particularly about 77% to about 90%, and especially about 80% to about 85% by weight of branched fatty acids, and less than about 30%, more preferably from about 5% to about 27%, particularly about 10% to about 23%, and especially about 15% to about 20% by weight of linear fatty acids, based on the total weight of fatty acids present in the ester of the lamellar membrane blend.

The branched fatty acid component of the ester preferably comprises alkyl side branches (attached directly to a carbon atom of the longest linear chain) having on average less than 3, more preferably less than 2.5, particularly in the range from 1.05 to 2, and especially 1.1 to 1.4 carbon atoms, i.e. the side branches are predominantly methyl groups. In a preferred embodiment, greater than 50%, more preferably greater than 60%, particularly in the range from 70% to 97%, and especially 80% to 93% by number of the side-branched groups are methyl groups. In a further preferred embodiment, greater than 30%, more preferably greater than 40%, particularly in the range from 45% to 90%, and especially 50% to 80% by number of the branched fatty acids contain single methyl side branches.

Suitable branched chain fatty acids for use in the ester of the lamellar membrane blend include iso-acids such as isostearic acid, isopalmitic acid, isomyristic acid, isoarachidic acid and isobehenic acid, neo-acids such as neodecanioc acid, and/or anti-iso acids. In an embodiment, the branched chain fatty acid is an iso-acid. Suitably, the fatty acid for use in the ester of the lamellar membrane blend is isostearic acid.

The branched fatty alcohol component of the ester is suitably a C12 to C30 branched or straight chain fatty alcohol. In one embodiment, the C12 to C30 chain is branched. In another embodiment the component is a C14 to C26 branched or straight chain fatty alcohol. In one embodiment, the C14 to C26 chain is branched. In another embodiment it is a C16 to C22 branched or straight chain fatty alcohol. In one embodiment, the C16 to C22 chain is branched. In yet another embodiment it is a C18 branched or straight chain fatty alcohol. In one embodiment, the C18 chain is branched.

Preferably, the branched fatty alcohol component of the ester is made from the fatty acid component of the ester. Therefore, suitably the same preferences apply to the branched fatty alcohol component of the ester as to the branched fatty acid component of the ester. In one embodiment the chain length of the fatty alcohol component of the ester is the same as the chain length of the fatty acid component of the ester. In another embodiment the chain length of the fatty alcohol component of the ester is the not the same as the chain length of the fatty acid component of the ester.

A mixture of branched and linear fatty alcohols may be present in the fatty alcohol component of the ester. Preferably, the fatty alcohol mixture comprises greater than 70%, more preferably in the range from 73% to 95%, particularly 77% to 90%, and especially 80% to 85% by weight of branched fatty alcohols, and less than 30%, more preferably in the range from 5% to 27%, particularly 10% to 23%, and especially 15% to 20% by weight of linear fatty alcohols, both based on the total weight of fatty alcohol present in the ester of the lamellar membrane blend.

Suitable branched fatty alcohols for use in the ester of the lamellar membrane blend include iso-alcohols such as isostearyl alcohol, isotetradecanol, isocetyl alcohol, isoarachidyl alcohol, isobehenyl alcohol and isolignoceryl alcohol; neo-alcohols such as neocapric alcohol; and/or anti-iso alcohols. In one embodiment, the branched chain fatty alcohol for use in the ester of the lamellar membrane blend is an iso-alcohol. In one embodiment, the ester of the iso-alcohol is isostearyl alcohol.

In one embodiment, the ester is an ester of a C16 to C22 branched fatty acid and a C16 to C22 branched fatty alcohol. The branched fatty acid and branched fatty alcohol may comprise the same number of carbon atoms, or a different number of carbon atoms. In one embodiment, the branched fatty acid and branched fatty alcohol comprise the same number of carbon atoms.

The ester may comprise one or more variations selected from the group comprising mono-branched fatty acid and poly-branched fatty alcohol, mono-branched fatty acid and mono-branched fatty alcohol, poly-branched fatty acid and mono-branched fatty alcohol, and poly-branched fatty acid and poly-branched fatty alcohol. The ester may be selected from this group by any suitable separation method. For example, the selected ester may be selected from a mixture of esters using a clathration method.

Exemplary branched fatty alcohols for use in the ester include, but are not limited to iso-alcohols such as isostearyl alcohol, isotetradecanol, isocetyl alcohol, isoarachidyl alcohol, isobehenyl alcohol and isolignoceryl alcohol; neo-alcohols such as neocapric alcohol; and/or anti-iso alcohols. In one embodiment, the fatty alcohol for use in the ester is isostearyl alcohol.

In an embodiment, the ester is an ester of a $C_{16}$ to $C_{30}$ branched fatty acid and a $C_{16}$ to $C_{30}$ branched fatty alcohol.

In one embodiment, the ester comprises a C18 mono- and/or poly-branched fatty acid and a C18 mono- and/or poly-branched fatty alcohol. In one embodiment, the ester is isostearyl isostearate.

In another embodiment, the ester is an ester of a $C_{16}$ to $C_{30}$ straight chain fatty acid and a $C_{16}$ to $C_{30}$ straight chain fatty alcohol.

In an embodiment, the ester is heptadecanoyl heptadecanoate ("HDHD").

Suitably, the ester is present in the lamellar membrane blend in an amount from about 1% to about 75% by weight, preferably from about 5% to about 50% by weight, more preferably from about 5% to about 35% by weight, based on the total weight of the lamellar membrane blend. In one embodiment, the ester is present in the lamellar membrane blend in an amount from about 1% to about 25% by weight, based on the total weight of the lamellar membrane blend.

Suitably, the ester of a branched fatty acid and a branched fatty alcohol and the alkyl amphiphilic component are present in the lamellar membrane blend at a ratio by weight of about 10:1 to about 1:10, preferably about 5:1 to about 1:5, more preferably about 5:1 to about 1:1.

Fatty Acid

The lamellar membrane blend further comprises a fatty acid or a mixture thereof. The fatty acid is suitably a C12 to C32 carbon fatty acid. In one embodiment, the fatty acid is a C16 to C30 fatty acid. In another embodiment, the acid is a C18 to C28 fatty acid. In another embodiment, the acid is a C18 to C24 fatty acid. The fatty acid may be branched or linear. In one embodiment, the fatty acid is linear.

Fatty acids suitable for use in the lamellar membrane blend can be obtained from the same natural sources as the branched fatty acid component of the ester.

A mixture of fatty acids may be present in the lamellar membrane blend. Preferably, when present, the fatty acid mixture comprises greater than 70%, more preferably in the range from 73% to 95%, particularly 77% to 90%, and especially 80% to 85% by weight of linear fatty acids, and less than 30%, more preferably in the range from 5% to 27%, particularly 10% to 23%, and especially 15% to 20% by weight of branched fatty acids, both based on the total weight of fatty acids present.

Suitable fatty acids for use in the lamellar membrane blend include lauric acid, myristic acid, palmitic acid, stearic acid, arachidic acid, behenic acid, lignoceric acid and cerotinic acid.

In one embodiment, the fatty acid is selected from the group consisting of stearic acid, arachidic acid, behenic acid, lignoceric acid and cerotinic acid, more preferably from the group consisting of arachidic acid, behenic acid and lignoceric acid. In another embodiment, the fatty acid is stearic acid or behenic acid. In yet another embodiment, the fatty acid is behenic acid.

Suitably, the fatty acid or mixture thereof is present in the lamellar membrane blend in an amount from about 1% to about 75% by weight. In one embodiment, the fatty acid or mixture is present from about 5% to about 50% by weight. In another embodiment, the fatty acid or mixture is present from about 5% to about 35% by weight, based on the total weight of the lamellar membrane blend. In yet another embodiment, the fatty acid or mixture thereof is present in the lamellar membrane blend in an amount from about 5% to about 25% by weight, based on the total weight of the lamellar membrane blend.

The fatty acid, or mixture of fatty acids, is present relative to the ester of a branched fatty acid and a branched fatty alcohol in a weight ratio of about 10:1 to about 1:10, preferably from about 5:1 to about 1:5, more preferably from about 2:1 to about 1:2. Desirably, the fatty acid, or mixture of fatty acids, and the ester of a branched fatty acid and a branched fatty alcohol are present in the blend at a weight ratio of about 1:1.

The fatty acid, or mixture of fatty acids, is present relative to the alkyl amphiphilic component at a weight ratio from about 10:1 to about 1:10, preferably from about 5:1 to about 1:5, more preferably from about 5:1 to about 1:1.

Fatty Alcohol

The lamellar membrane blend further comprises at least one fatty alcohol which may be saturated or unsaturated, branched or straight (linear) chain. In one embodiment, the fatty alcohol is linear. In another embodiment, the fatty alcohol is branched.

In an embodiment, the fatty alcohol is selected from a C12 to C36 branched or straight chain fatty alcohol. In another embodiment, the fatty alcohol is selected from a C12 to C30 branched or straight chain fatty alcohol. In another embodiment, the fatty alcohol is selected from a C14 to C26 branched or straight fatty alcohol. In one embodiment, the $C_{14}$-$C_{26}$ chain is branched. In another embodiment it is a $C_{16}$ to $C_{22}$ branched or straight chain fatty alcohol. In yet another embodiment, the fatty alcohol is selected from a C16 to C24 branched or straight fatty alcohol. In one embodiment, the $C_{16}$ to $C_{22}$ chain is branched. In another embodiment, the fatty alcohol is a branched or straight chain $C_{20}$-$C_{26}$ fatty alcohol. In one embodiment, the $C_{20}$-$C_{26}$ chain is branched. In yet another embodiment the fatty alcohol is a $C_{18}$ or $C_{22}$ or $C_{24}$ branched or straight chain fatty alcohol. In one embodiment, the $C_{18}$ or $C_{22}$ or $C_{24}$ chain is branched.

In a particular embodiment, the fatty alcohol is a mixture of two or more fatty alcohols. In an embodiment, the fatty alcohol comprises two or more fatty alcohols selected from the group consisting of C12 to C28 fatty alcohols. In another embodiment, the fatty alcohol comprises two or more fatty alcohols selected from the group consisting of C14 to C26 fatty alcohols. In yet another embodiment, the fatty alcohol comprises two or more fatty alcohols selected from the group consisting of C16 to C24 fatty alcohols.

In an embodiment, at least one of the fatty alcohols are within 4 carbon atoms of the alkyl chain length of the alkyl amphiphilic component in the composition. In another embodiment, at least one of the fatty alcohols is within 2 carbon atoms of the alkyl chain length of the alkyl amphiphilic component in the composition. In yet another embodiment, at least one of the fatty alcohols is the same as the alkyl chain length of the alkyl amphiphilic component.

Exemplary fatty alcohols include, but are not limited to, decyl alcohol, lauryl alcohol, tridecyl alcohol, myristyl alcohol, pentadecyl alcohol, cetyl alcohol, isocetyl alcohol, cetearyl alcohol, palmitoleyl alcohol, heptadecyl alcohol, stearyl alcohol, isostearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, lacceryl alcohol, geddyl alcohol, tetratriacontanol, lanolin alcohol and palm alcohol, and mixtures thereof. In one embodiment, the fatty alcohol is behenyl alcohol, cetyl alcohol, stearyl alcohol or mixtures thereof. In one embodiment, the fatty alcohol is behenyl alcohol. In another embodiment, the fatty alcohol is cetyl alcohol.

In one embodiment, the fatty alcohol is lauryl alcohol, tridecyl alcohol, myristyl alcohol, pentadecyl alcohol, cetyl alcohol, cetearyl alcohol, palmitoleyl alcohol, heptadecyl alcohol, stearyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, and mixtures thereof.

In one embodiment, the fatty alcohol is a mixture of cetyl alcohol and one or more selected from the group consisting of cetearyl alcohol, palmitoleyl alcohol, heptadecyl alcohol, stearyl alcohol, nonadecyl alcohol, arachidyl alcohol, heneicosyl alcohol, behenyl alcohol, erucyl alcohol and lignoceryl alcohol.

In another embodiment, the fatty alcohol is a mixture of cetearyl alcohol and one or more selected from the group consisting of palmitoleyl alcohol, heptadecyl alcohol, stearyl alcohol, nonadecyl alcohol, arachidyl alcohol, heneicosyl alcohol, behenyl alcohol, erucyl alcohol and lignoceryl alcohol.

In one embodiment, the fatty alcohol is a mixture of cetyl alcohol and cetearyl alcohol.

In another embodiment, the fatty alcohol is a mixture of cetyl alcohol and behenyl alcohol. In yet another embodiment, the fatty alcohol is a mixture of cetearyl alcohol and behenyl alcohol.

In a further embodiment, the fatty alcohol is a mixture of cetyl alcohol and lignoceryl alcohol.

In yet a further embodiment, the fatty alcohol is a mixture of cetearyl alcohol and lignoceryl alcohol.

In an embodiment, the fatty alcohol or mixture thereof is present in the lamellar membrane blend in an amount from about 45% to about 85% by weight, or from about 50% to about 75% by weight, based on the total weight of the lamellar membrane blend.

In one embodiment, the fatty alcohol or mixture thereof is present in the in the lamellar membrane blend, in an amount from about 2.5% to about 10% by weight, based on the total weight of the composition.

The fatty alcohol, or mixture of fatty alcohols, and the fatty acid, or mixture of fatty acids may react to form an ester when both present in the lamellar membrane blend. Preferably, the ester, when formed, is a cetyl behenate or cetyl stearate ester.

In an embodiment, the fatty alcohol, or mixture of fatty alcohols, is present relative to the alkyl amphiphilic component at a weight ratio of about 20:1 to about 2:1. In another embodiment, the fatty alcohol, or mixture of fatty alcohols, is present relative to the alkyl amphiphilic component at a weight ratio of about 15:1 to about 5:1.

Phospholipid

The compositions of the invention may optionally comprise a phospolipid. In one embodiment, the phospholipid is hydrogenated lecithin. In another embodiment, the phospholipid is phosphatidylcholine. In yet another embodiment, the phospholipid is hydrogenated phosphatidylcholine. In a further embodiment, the phospholipid is a mixture of phosphatidylcholine and hydrogenated phosphatidylcholine.

Lamellar Membrane Blend

The lamellar membrane blend may be made in accordance with the disclosure of WO 2012/104604, Pennick et al., and US 2013/0324499, Pennick et al., whose disclosures are incorporated herein by reference.

In one embodiment of the disclosure, there is provided a lamellar membrane blend for use in a topical composition, the lamellar membrane blend comprising (i) an alkyl amphiphilic component, (ii) an ester of a branched fatty acid and a branched fatty alcohol, (iii) a fatty acid, and (iv) a fatty alcohol. In an embodiment, the fatty alcohol is a mixture of two or more fatty alcohols.

In an embodiment, the lamellar membrane blend comprises potassium dicetyl phosphate, isostearyl isostearate, behenic acid, cetyl alcohol and behenyl alcohol.

In another embodiment, the lamellar membrane blend comprises potassium dicetyl phosphate isostearyl isostearate, stearic acid, cetyl alcohol and behenyl alcohol.

In yet another embodiment, the lamellar membrane blend comprises potassium dicetyl phosphate, isostearyl isostearate, behenic acid, cetyl alcohol and cetearyl alcohol.

In a further embodiment, the lamellar membrane blend comprises potassium dicetyl phosphate isostearyl isostearate, stearic acid, cetyl alcohol and cetearyl alcohol.

The above noted lamellar membrane blends may each further comprise potassium monocetyl phosphate.

In yet a further embodiment, the lamellar membrane blend comprises potassium monocetyl phosphate, isostearyl isostearate, behenic acid, cetearyl alcohol and behenyl alcohol.

The lamellar membrane blend may optionally comprise a phospholipid.

In an alternative embodiment the lamellar membrane blend may be comprised of (i) a mono alkyl amphiphilic component, (ii) an ester of a branched fatty acid and a branched fatty alcohol, (iii) a fatty acid, and (iv) a fatty alcohol. In an embodiment, the fatty alcohol is a mixture of two or more fatty alcohols.

In this embodiment, the lamellar membrane blend comprises potassium monocetyl phosphate, isostearyl isostearate, behenic acid, cetyl alcohol and cetearyl alcohol.

In a further embodiment, the lamellar membrane blend comprises potassium monodicetyl phosphate, isostearyl isostearate, stearic acid, cetyl alcohol and cetearyl alcohol.

In yet a further embodiment, the lamellar membrane blend comprises potassium monocetyl phosphate, isostearyl isostearate, behenic acid, cetyl alcohol and behenyl alcohol.

The above lamellar membrane blends may each optionally comprise a phospholipid.

In one embodiment of the disclosure, there is provided a lamellar membrane blend for use in a topical composition, the lamellar membrane blend comprising (i) a mixture of monocetyl potassium phosphate and potassium dicetyl phosphate, (ii) an ester of a branched fatty acid and a branched fatty alcohol, (iii) a fatty acid, and (iv) a fatty alcohol. In an embodiment, the fatty alcohol is a mixture of two or more fatty alcohols.

In an embodiment, the lamellar membrane blend comprises a mixture of monocetyl potassium phosphate and potassium dicetyl phosphate, isostearyl isostearate, behenic acid, cetyl alcohol and behenyl alcohol.

In another embodiment, the lamellar membrane blend comprises a mixture of monocetyl potassium phosphate and potassium dicetyl phosphate, isostearyl isostearate, stearic acid, cetyl alcohol and behenyl alcohol.

In yet another embodiment, the lamellar membrane blend comprises a mixture of monocetyl potassium phosphate and potassium dicetyl phosphate, isostearyl isostearate, behenic acid, cetyl alcohol and cetearyl alcohol.

In a further embodiment, the lamellar membrane blend comprises a mixture of monocetyl potassium phosphate and potassium dicetyl, isostearyl isostearate, stearic acid, cetyl alcohol and cetearyl alcohol.

Dermatologically Acceptable Excipients

All of the compositions of the invention may further comprise at least one dermatologically acceptable excipient.

In an embodiment, the dermatologically acceptable excipient is selected from the group consisting of an antioxidant, a chelating agent, a preservative, a colorant, a sensate, a moisturizer, a humectant, and a pH adjusting agent, and mixtures thereof.

In an embodiment, the compositions of the invention are free or substantially free of a conventional emulsifier.

Antioxidant

The compositions of the invention may further comprise an antioxidant. In an embodiment, the antioxidant is a mixture of two or more antioxidants.

Antioxidants may protect the composition from oxidation (e.g. becoming rancid) and/or may also provide lip conditioning benefits upon application to the lips. Tocopherol, tocopheryl acetate, some botanical butters, niacinamide, pterostilbene (trans-3,5-dimethoxy-4-hydroxystilbene) magnolol, and green tea extracts, alone or in combination thereof are exemplary natural product antioxidants suitable for use in the compositions. Other suitable antioxidants include ascorbic acid and esters thereof such as ascorbyl palmitate, butylated hydroxytoluene (BHT), butylated hydroxyanisole (BHA), propyl gallate, vitamin E TPGS, ethyl ferulate, ferulic acid, resveratrol, 2,2-dimethyl chroman (Lipochroman®), singapine, tetrahydrocurcumin or other curcumin derivatives, hydroxytyrosol, Bis-Ethylhexyl Hydroxydimethoxy Benzylmalonate (Ronacare AP 0), dimethylmethoxy chromanyl palmitate (Chromabright®) or a combination or mixture thereof. It is recognized that a combination or mixture of all of these antioxidants is also suitable for use herein. In one embodiment, the antioxidant is tocopherol, or a mixture of tocopherol and ascorbyl palmitate. In another embodiment, the antioxidant is niacinamide. Suitably, the antioxidant is present in an amount from about 0.001% to about 1% by weight, based on the total weight of the composition.

Chelating Agents

The compositions of the invention may further comprise a chelating agent. In an embodiment, the chelating agent is a mixture of two or more chelating agents.

Exemplary chelating agents include, but are not limited to, citric acid, glucuronic acid, sodium hexametaphosphate, zinc hexametaphosphate, ethylenediamine tetraacetic acid (EDTA), ethylenediamine disuccinic acid (EDDS), phosphorates, salts thereof, or a combination or mixture thereof.

In one embodiment, the chelating agent is EDTA or a salt thereof, such as potassium, sodium or calcium salts of EDTA. In another embodiment, the chelating agent is ethylenediamine succinic acid or a salt thereof, such as potassium, sodium or calcium salts.

In one particular embodiment, the chelating agent is trisodium ethylenediamine disuccinate.

Suitably, the chelating agent is present in an amount from about 0.05% to about 1% by weight, based on the total weight of the composition.

Preservative

The compositions of the invention may further comprise a preservative. In an embodiment, the preservative is a mixture of two or more preservatives.

Exemplary preservatives include, but are not limited to, benzyl alcohol, diazolidinyl urea or other substituted ureas and hydantoin derivatives, methyl paraben, ethyl paraben, propyl paraben, butyl paraben, phenoxyethanol, sorbic acid, benzoic acid, salts thereof, or a combination or mixture thereof.

Suitably, the preservative is present in an amount from about 0.01% to about 2% by weight. In an alternative embodiment, the compositions of the invention are free of conventional preservatives.

In an embodiment, the preservative is a combination of non conventional preservatives, such as capryloyl glycine, 1,2-hexanediol and other glycols. Other suitable glycols include, but are not limited to, caprylyl glycol and/or pentylene glycol.

In one embodiment, the preservative is selected from the group consisting of capryloyl glycine, caprylyl glycol, pentylene glycol and 1,2-hexanediol, and mixtures thereof.

Suitably, these preservatives are present in an amount from about 0.5% to about 5% by weight, based on the total weight of the composition. In one embodiment, the capryloyl glycine is present in an amount from about 0.5% to about 2% by weight and the additional glycols can be added in amounts up to 5% by weight, based on the total weight of the composition. Suitably, the preservative is a combination of at least capryloyl glycine and caprylyl glycol in an amount from about 0.5% to about 2% by weight, based on the total weight of the composition.

Colorant

The compositions of the invention may further comprise a colorant that imparts color to the composition. Colorants include, for example, natural colorants such as plant extracts, natural minerals, carmine, synthesized and/or processed colorant materials such as iron oxides, synthetic dyes, organic compounds, lake colorants, and FDA certified colorants for use on the skin. The above list is not an exhaustive list of colorants and those of skill in the art may consider the use of other colorants. Formulations of colorants are commercially available. An example of a commercially available colorant contains caprylic/capric triglycerides (59.5%), titanium dioxide (39.6%), castor oil phosphate (0.5%) and triethoxycaprylylsilane (0.4%).

Sensate

The compositions of the invention may further comprise a sensate. A sensate is a composition that initiates a sensory perception such as heating or cooling, for example, when contacted with the skin. Exemplary sensates include, but are not limited to, mint extracts, cinnamon extract and capsaicin. Preferred sensates are derived from natural sources. However, synthetic sensates are within the scope of this invention. Sensates typically have high potency and accordingly may yield significant impact at low levels. Suitably, the sensate is present in an amount from about 0.05% to about 5% by weight, based on the total weight of the composition.

Moisturizer

The compositions of the invention may further comprise a moisturizer. Exemplary moisturizers useful in the present compositions include, but are not limited to, pentylene glycol, butylene glycol, polyethylene glycol, sodium pyrrolidone carboxylate, α-hydroxy acids, β-hydroxy acids, polyhydric alcohols, ethoxylated and propoxylated polyols, polyols, polysaccharides, panthenol, hexylene glycol, propylene glycol, dipropylene glycol, sorbitol, hyaluronic acid and salts thereof, such as sodium, potassium or calcium salts, and mixtures thereof.

Suitably, the moisturizer is present in an amount from about 0.5% to about 10% by weight, based on the total weight of the composition.

Humectant

The compositions of the invention may comprise a humectant. Exemplary humectants useful in the present compositions include, but are not limited to, glycerin, betaine, sarcosine, propylene glycol, butylene glycol, pentylene glycol, hexylene glycol, caprylyl glycol, sorbitol, glucose, and mixtures thereof. In one embodiment, the humectant is a mixture of glycerin, pentylene glycol, caprylyl glycol and glucose. In another embodiment, the humectant is a mixture of glycerin and pentylene glycol.

Suitably, the humectant is present in an amount from about 1% to about 15% by weight, based on the total weight of the composition.

pH Adjusting Agent

The compositions of the invention may further comprise a pH adjusting agent. In one embodiment, the pH adjusting agent is a base. Suitable bases include amines, bicarbonates, carbonates, and hydroxides such as alkali or alkaline earth metal hydroxides, as well as transition metal hydroxides. In an embodiment, the base is sodium hydroxide or potassium hydroxide.

In another embodiment, the pH adjusting agent is an acid, an acid salt, or mixtures thereof. Suitably, the acid is selected from the group consisting of lactic acid, acetic acid, maleic acid, succinic acid, citric acid, benzoic acid, boric acid, sorbic acid, tartaric acid, edetic acid, phosphoric acid, nitric acid, ascorbic acid, dehydroacetic acid, malic acid, propionic acid, sulphuric acid and hydrochloric acid, or a combination or mixture thereof.

In yet another embodiment, the pH adjusting agent is a buffer. Suitably, the buffer is selected from the group consisting of citrate/citric acid, acetate/acetic acid, phosphate/phosphoric acid, propionate/propionic acid, lactate/lactic acid, carbonate/carbonic acid, ammonium/ammonia and edetate/edetic acid, or a combination or mixture thereof.

Pharmaceutically Active Agent

The compositions of the invention may further comprise a pharmaceutically acceptable active agent. Exemplary pharmaceutically active agents include, but are not limited to, an anti-inflammatory agent, an antibacterial agent, an antiviral agent, an antifungal agent, an anti-parasitic, a nutritional agent, a sunscreen, a sunblock, and mixtures thereof. Suitably, the pharmaceutically active agent is present in an amount from about 0.001% to about 30% by weight, depending on the nature of the active agent, the condition being treated, and the composition.

In one embodiment, the pharmaceutically active agent is an anti-inflammatory agent. Exemplary anti-inflammatory agents are niacinamide and N-acylalkanolamines including, but not limited to, lactamide monoethanolamide (MEA), oleamide MEA, acetamide MEA (AMEA), palmitioyl MEA (PMEA), N-acetylphosphatidylethanolamine, N-acetylethanolamine, N-oleoylethanolamine, N-linolenoylethanolamine, N-acylethanolamine, and N-acyl-2-hydroxy-propylamine.

In one embodiment, the N-acylalkanolamine is palmitidyl MEA (PMEA).

Suitably, the N-acylalkanolamine is present in an amount from about 0.01% to about 2% by weight, based on the total weight of the composition.

In another embodiment, the anti-inflammatory agent is niacinamide.

Suitably, the niacinamide is present in an amount from about 0.01% to about 5% by weight, based on the total weight of the composition.

In another embodiment, the pharmaceutically active agent is a sunscreen. Suitably, the sunscreen is a UVA and/or UVB sunscreen. Suitably, the sunscreen is a combination of a UVA sunscreen and a UVB sunscreen.

Efficacious protection from UVA and UVB radiation requires the use of significant amounts of sunscreen, and often a mixture of organic sunscreens, to achieve efficacious protection from both UVA and UVB radiation. UVB radiation, which is radiation in the wavelength range of 290 nm-320 nm, has traditionally been characterized as the radiation that causes sunburn. In addition, UVB radiation can decrease enzymatic and non-enzymatic antioxidants in the skin and impair the natural protective mechanisms in the skin, thereby contributing to DNA damage and potentially skin cancer. The dangers of UVA radiation, which is radiation in the wavelength range of 320 nm to 400 nm, have only recently been recognized. Chronic exposure to UVA radiation can cause damage to gene P53 DNA, possibly leading to cancer. Additionally, the longer UVA wavelengths allow for relatively deep penetration into the skin tissues causing damage to the elastic fibers and collagen which give skin its shape, thus causing wrinkling and eventually premature skin aging. Thus, protecting the skin from UVA and UVB radiation is important for skin health and overall health more generally.

For purposes herein wavelength range is as follows: UVA1: 340-400 nm, UVA2: 320-340 nm, and UVB: 290-. Suitable UVA1 and UVA2 filters include, but are not limited to, Avobenzone (Butyl methoxy dibenzoyl methane) (Parsol 1789, Eusolex 9020), Bisdisulizole disodium (Neo Heliopan AP), Diethylamino hydroxybenzoyl hexyl benzoate (Uvinul A Plus), Drometrizole trisiloxane (Mexoryl XL), Menthyl anthranilate (Meradimate), oxybenzone, sulisobenzene and dioxybenzone, and mixtures thereof.

UVB filters include, but are not limited to, Amiloxate, 4-Aminobenzoic acid (PABA), Cinoxate, Ethylhexyl triazone/octyltriazone (Uvinul T 150), Homosalate, 4-Methylbenzylidene camphor (Parsol 5000), Octyl methoxycinnamate (Octinoxate) (Parsol MCX), Octyl salicylate/ethylhexyl salicylate (Octisalate), Padimate O (Escalol 507), Phenylbenzimidazole sulfonic acid (Ensulizole), Polysilicone-15 (Parsol SLX), Enzacamene, and Trolamine salicylate, and mixtures thereof.

UVA+UVB filters include, but are not limited to, Bemotrizinol (Tinosorb S), Benzophenones 1-12, Dioxybenzone, -Terephthalylidene dicamphor sulfonic acid (Ecamsule) (Mexoryl SX), Diethylhexyl butamido triazone/Iscotrizinol (Uvasorb HEB), Octocrylene, Oxybenzone (Eusolex 4360), Benzophenone-4(Sulisobenzone), Bisoctrizole (Tinosorb M), Heliolex (a combination of avobenzone and oxybenzone), Phenylbenzimiazole sulfonic acid (Ensulizole), Benzophenone-8, and mixtures thereof.

Other exemplary sunscreens useful in the present invention (with maximum suitable amounts of each sunscreen in % wt/wt) include, but are not limited to, amino benzoic acid (about 15%), Avobenzone (about 3%), cinoxate (about 3%), octyl methoxycinnamate (Octinoxate) (about 10%), homosalate (about 15%), meradimate (about 5%), octocrylene (about 10%), ethylhexyl salicylate (also known as octyl salicylate or octisalate) (about 5%), oxybenzone (about 6%), dioxybenzone (about 3%), Octyldimethyl PABA (Padimate 0) (about 8%), p-amyldimethyl PABA (Padimate A) (about 3%), Phenylbenzimidazole sulfonic acid (ensulizole)(about 4%), sulisobenzene (about 10%), trolamine salicylate (about 12%), benzophenone (about 10%), benzylidine compounds, such as 4-methylbenzylidine camphor (Parsol 5000) (about 6%), butyl methoxydibenzoylmethane (about 5%), bis-ethylhexyloxyphenol methoxyphenyl triazine (Bemotrizinol or Tinosorb S) (about 10%), camphor benzalkonium methosulfate (about 6%), diethyl amino hydroxy benzoyl hexyl benzoate (Uvinul A plus) (about 10%), diethylhexyl butamido triazine (Uvasorb HEB) (about 10%), disodium phenyl dibenzylmidazole tetrasulfonate (Bisdisulizole disodium or NeoHeliopan AP) (about 10%), drometrizole trisiloxane (silatriazole or Mexoryl XL) (about 15%), ethylhexyl dimethyl para-amino benzoic acid (about 8%), ethylhexyl methoxycinnamate (about 10%), ethylhexyl Triazone (Uvinul T 150) (about 5%), isoamyl p-methoxycinnamate (about 10%), 4-methylbenzylidene camphor (about 10%), methylene bis-benzotriazolyl tetramethylbutylphenol (Bisoctrizole or Tinosorb M) (about 10%), PEG-25 paramainobenzoic acid (about 5%), phenylbenziamido methylbenzylidene camphor (about 6%), diisopropyl methyl cinnamate (about 10%), dimethoxyphenyl-[1-(3,4)-4,4-dimethyl]1,3 pentanedione (about 7%), ethylhexyl dimethyloxy benzylidene dioxoimidazoline propionate (about 3%), ferulic acid (about 10%), glyceryl ethylhexanoate dimethoxycinnamate (about 10%), glycerol para-aminobenzoic acid (about 10%), phenylbenzimidazole sulfonic acid (about 3%) and Parsol SLX (benzylidene malonate polysiloxane), and mixtures thereof. The amounts listed in the preceding list are for each sunscreen individually. In some embodiments in which a combination or mixture of sunscreens is used, the total combined amount of a sunscreen may be less or equal to the sum of the maximum suitable amounts for each individual sunscreen.

As used herein, the term "Cinnamates", include octinoxate, cinoxate, and isoamyl p-methoxy cinnamate.

As used herein, the term "Salicylates" include octisalate, homosalate, and trolamine salicylate.

As used herein, the term "Benzophenones" includes oxybenzone, sulisobenzone, and dioxybenzone.

As used herein, the term "PABA and derivatives" includes PABA (p-aminobenzoic acid), Octyldimethyl PABA (Padimate O), p-amyldimethyl PABA (Padimate A), Ethyl 4[bis (hydroxypropyl)] aminobenzoate, and glyceryl PABA.

Avobenzone, and benzophenones, as well as some other sunscreens, are photo unstable. Therefore these sunscreens are frequently combined with other sunscreens or stabilizers to increase the photostability of the final product. Some suitable photo stabilizers also referred to herein as boosters, include, but are not limited to Octocrylene, Diethylhexyl 2,6-naphthalate, and Diethylhexyl syringylidene malonate. In one embodiment, the photostabilizer is Diethylhexyl syringylidene malonate.

Although a single sunscreen may be used in a composition, typically a combination of sunscreens will be used as each sunscreen has a characteristic wavelength range in which it absorbs UV radiation (UVR) and typically that range is less than the entire range for which protection is desired. Thus, use of a combination of sunscreens provides protection over a wider range of wavelengths. Additionally, efficacy of protection is also related to the amount of sunscreen. As regulatory agencies limit the amount of each sunscreen that can be used, the use of multiple sunscreens improves the SPF while maintaining regulatory compliance.

Organic sunscreens and their efficacious wavelength range (along with suitable amounts) are as follows: amino benzoic acid (260 nm-313 nm, about 5% to about 15%); padimate 0 (290 nm-315 nm, about 1.4% to about 8%); dioxybenzone (260 nm-380 nm, about 1% to about 3%); oxybenzone (270 nm-350 nm, about 2% to about 6%); sulisobenzone (260 nm -375 nm, about 5% to about 10%); cinoxate (270 nm-328 nm, about 1% to about 3%); octocrylene (250 nm-360 nm, about 7% to about 10%); Avobenzone (320 nm-400 nm, about 1% to about 3%); octyl salicylate (280 nm-320 nm, about 3% to about 5%); homosalate (295 nm-315 nm, about 4% to about 15%); trolamine salicylate (260 nm-320 nm, about 5% to about 12%); octinoxate (290 nm-320 nm, about 2% to about 7.5%).

In one embodiment, at least two sunscreens are used where the first sunscreen has an efficacious wavelength range that includes about 280 nm to about 315 nm and the second sunscreen has an efficacious wavelength range that includes about 315 nm to about 400 nm.

In one embodiment, the at least one UVA sunscreen is Avobenzone, and/or Diethylamino hydroxybenzoyl hexyl benzoate (Uvinul A Plus).

In an embodiment, the at least one UVB sunscreen is Ethylhexyl triazone (Uvinul T 150), Octyl methoxycinnamate (Octinoxate), and/or Octyl salicylate (Octisalate), alone or in mixtures thereof.

In an embodiment, the at least one sunscreen which is a UVA+UVB filter is Bemotrizinol (Tinosorb S), Iscotrizinol (Uvasorb HEB), Octocrylene, and Bisoctrizole (Tinosorb M), and mixtures thereof.

In one embodiment, the sunfilters include a combination of Bemotrizinol, Diethylamino hydroxybenzoyl hexyl benzoate, isoamyl p-methoxycinnamate, an optionally Tinosorb A2B.

In another embodiment, the sunfilters include a combination of Tinosorb S, Tinosorb M, and Octyl methoxycinnamate.

In another embodiment, the sunfilters include a combination of Tinosorb S, Tinosorb M, Octyl methoxycinnamate, and Uvinul A Plus.

In an embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol which is a mixture of cetyl alcohol and one or more selected from the group consisting of palmitoleyl alcohol, heptadecyl alcohol, stearyl alcohol, cetearyl alcohol, nonadecyl alcohol, arachidyl alcohol, heneicosyl alcohol, behenyl alcohol, erucyl alcohol, and lignoceryl alcohol; and
wherein in use the composition has a water vapor transmission rate of less than 65 g·m$^{-2}$·hr$^{-1}$ measured in vitro using modWVTR test methodology.

In one embodiment, the alkyl amphiphilic component may suitably be monocetyl potassium phosphate, potassium dicetyl phosphate or a mixture thereof. In another embodiment, the composition further comprises a phospholipid.

In another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol which is a mixture of cetearyl alcohol and one or more selected from the group consisting of palmitoleyl alcohol, heptadecyl alcohol, stearyl alcohol, nonadecyl alcohol, arachidyl alcohol, heneicosyl alcohol, behenyl alcohol, erucyl alcohol, and lignoceryl alcohol; and
wherein in use the composition has a water vapor transmission rate of less than 65 g·m$^{-2}$·hr$^{-1}$ measured in vitro using modWVTR test methodology.

In one embodiment, the alkyl amphiphilic component may suitably be monocetyl potassium phosphate, potassium dicetyl phosphate or a mixture thereof. In another embodiment, the composition further comprises a phospholipid.

In yet another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol which is a mixture of cetyl alcohol and behenyl alcohol; and
wherein in use the composition has a water vapor transmission rate of less than 65 g·m$^{-2}$·hr$^{-1}$ measured in vitro using modWVTR test methodology.

In one embodiment, the alkyl amphiphilic component may suitably be monocetyl potassium phosphate, potassium dicetyl phosphate or a mixture thereof. In another embodiment, the composition further comprises a phospholipid.

In a further embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol which is a mixture of cetearyl alcohol and behenyl alcohol; and
wherein in use the composition has a water vapor transmission rate of less than 65 g·m$^{-2}$·hr$^{-1}$ measured in vitro using modWVTR test methodology.

In one embodiment, the alkyl amphiphilic component may suitably be monocetyl potassium phosphate, potassium dicetyl phosphate or a mixture thereof. In another embodiment, the composition further comprises a phospholipid.

In an embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol or mixture of fatty alcohols which have a molar % in the composition of from about 50 to about 85 molar %; and
wherein in use the composition has a water vapor transmission rate of less than 65 g·m$^{-2}$·hr$^{-1}$ measured in vitro using modWVTR test methodology.

In one embodiment, the alkyl amphiphilic component may suitably be monocetyl potassium phosphate, potassium dicetyl phosphate or a mixture thereof. In another embodiment, the composition further comprises a phospholipid.

In another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component which is mono alkyl potassium cetyl phosphate and which has a molar % in the composition of from about 50 to about 85 molar %; (ii) an ester of a branched fatty acid and a branched fatty alcohol, (iii) a fatty acid, and (iv) a fatty alcohol or mixture of fatty alcohols which have a molar % in the composition of from about 50 to about 85 molar %; and wherein in use the composition has a water vapor transmission rate of less than 65 g·m$^{-2}$·hr$^{-1}$ measured in vitro using modWVTR test methodology.

In one embodiment, the composition further comprises a phospholipid.

In another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component which is mono alkyl potassium cetyl phosphate and which has a molar % in the composition of from about 50 to about 85 molar %; (ii) an ester of a branched fatty acid and a branched fatty alcohol, (iii) a fatty acid, and (iv) cetyl alcohol and a second fatty alcohol wherein the molar ratio of the second fatty alcohol to the amount of cetyl alcohol is from about 2:1 to about 0.5:1; and wherein in use the composition has a water vapor transmission rate of less than 65 g·m$^{-2}$·hr$^{-1}$ measured in vitro using modWVTR test methodology.

In one embodiment, the composition further comprises a phospholipid.

In one embodiment, the molar ratio of the second fatty alcohol to the amount of cetyl alcohol is from about 4:1 to about 0.3:1. In another embodiment, the molar ratio of the second fatty alcohol to the amount of cetyl alcohol is from about 2.0:1.0. In another, it is about 1.25:1.

In one embodiment, the second fatty alcohol is behenyl alcohol.

In another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, and (iv) a fatty alcohol; and wherein the molar ratio of the fatty alcohol to the fatty acid is from about 2.5:1 to about 19:1.0; and wherein in use the composition has a water vapor transmission rate of less than 65 g·m$^{-2}$·hr$^{-1}$ measured in vitro using modWVTR test methodology.

In another embodiment, the ratio is the molar ratio of the fatty alcohol to the fatty acid is from about 2.5:1 to about 15:1.0. In another embodiment, the ratio is the molar ratio of the fatty alcohol to the fatty acid is from about 2.5:1 to about 6:1.0.

In one embodiment, the alkyl amphiphilic component may suitably be monocetyl potassium phosphate, potassium dicetyl phosphate or a mixture thereof. In another embodiment, the composition further comprises a phospholipid.

In a further embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, (iv) a fatty alcohol, (v) phosphatidyl choline;
and the molar ratio of the alkyl amphiphilic component to the phosphatidyl choline is from about 35:1 to about 6:1, wherein in use the composition has a water vapor transmission rate of less than 65 g·m$^{-2}$·hr$^{-1}$ measured in vitro using modWVTR test methodology.

In one embodiment, the molar ratio is from about 10:1 to about 6:1. In another embodiment, the molar ratio is from about 9:1 to about 8:1.

In one embodiment, the alkyl amphiphilic component may suitably be monocetyl potassium phosphate, potassium dicetyl phosphate or a mixture thereof.

In a further embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) an alkyl amphiphilic component, (ii) an ester of a branched fatty acid and a branched fatty alcohol, (iii) a fatty acid, (iv) a fatty alcohol, (v) phosphatidyl choline present in a molar % of the of 2.0 to about 8%;

wherein in use the composition has a water vapor transmission rate of less than 65 g·m$^{-2}$·hr$^{-1}$ measured in vitro using modWVTR test methodology.

In one embodiment, the alkyl amphiphilic component may suitably be monocetyl potassium phosphate, potassium dicetyl phosphate or a mixture thereof.

In another embodiment, the composition has a molar % of the phosphatidyl choline (PC), if present of about 7 to about 8%.

In a further embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) monoalkyl potassium cetyl phosphate, (ii) an ester of a branched fatty acid and a branched fatty alcohol, (iii) a fatty acid, (iv) a fatty alcohol, (v) phosphatidyl choline present in a molar % of the of 6.0 to about 15%;

wherein in use the composition has a water vapor transmission rate of less than 65 g·m$^{-2}$·hr$^{-1}$ measured in vitro using modWVTR test methodology.

In one embodiment, the molar % is from about 6 to about 9%. In yet another embodiment, the mol % is from about 6 to about 7%.

In a further embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) monoalkyl potassium cetyl phosphate, (ii) an ester of a branched fatty acid and a branched fatty alcohol, (iii) a fatty acid, (iv) a fatty alcohol, (v) phosphatidyl choline, and the molar ratio of the fatty alcohol to the phosphatidyl choline is from about 20:1 to about 7:1, wherein in use the composition has a water vapor transmission rate of less than 65 g·m$^{-2}$·hr$^{-1}$ measured in vitro using modWVTR test methodology.

In another embodiment, the molar ratio is from about 9:1 to about 4.3 to 1.

In all of the above combinations, the composition may further comprise at least one dermatologically acceptable excipient selected from an antioxidant, a chelating agent, a preservative, a colorant, a sensate, a moisturizer, a humectant, a pH adjusting agent, a pharmaceutically acceptable agent, and combinations and mixtures thereof.

The compositions of the invention comprise at least one lamellar membrane structure. Generally this refers to a planar lipid bilayer sheet, or a slight curve around a droplet of oil. They may also exist as separate discrete lamellae in the bulk aqueous phase. This is in contrast to a rounded formed liposomal structure. In another embodiment, the respective lamellar membrane structures form two or more stacked lamellar membrane structures, sometimes referenced as a liquid crystal. Two lamellar membrane structures stacked together, one on top of the other, is known as a double lamellar membrane structure.

FIG. 1 illustrates the key physical difference between an oil in water emulsion that can form a lamellar structure (A) and a liposome (B). In an O/W emulsion the surfactant-emulsifiers orientate so that the hydrophilic heads face out into the continuous phase and the hydrophobic tails are anchored within the oil droplet. In the case of a liposome, these are typically aqueous filled cores where the hydrophilic heads of the interfacial layer of surfactant-emulsifer (here shown as a dialkyl phospholipid which can form liposomal structures) orientated toward the hydrophilic aqueous core and for the outermost layer, orientated towards the continuous phase.

Even if systems contain lamellar forming ingredients such as those further described herein, those systems can be prepared in a manner that will yield either a liposome or O/W emulsion. The physical characteristics of each system is different and is outlined below.

| Property | O/W Emulsion | Aqueous Core Liposome |
| --- | --- | --- |
| Droplet size | Typically >1000 nm | Range from 25 nm to 500 nm |
| Opacity | Very often white in appearance due to greater interaction with visible light. | Can be translucent to blue due to wavelength of light absorption/reflection |
| Rheology/Viscosity | Mid to high viscosity system (attributable to long range interactions between droplets) | Tend towards low viscosity systems (limited long range interactions between systems) |
| Dynamic Lamellar Structure (Viscosity Building) | Viscosity can build post manufacture due to thermodynamic equilibration. Lamellar structure builds with time causing an increase in viscosity. | Viscosity is relatively stable as lamellar structure has been established during the manufacturing process. |

The properties described above are measurable using standard lab measurement methods available in the art. All of these properties will clearly provide for an accurate designation of those O/W emulsions (microscopy, rheology, visual assessment) having lamellar structures (e.g. with FTIR/XRD).

It should be noted that the present formulations do not include as a necessary excipient a traditional surfactant. Thus in one embodiment, the formulations of the present invention can include small amounts, e.g., 0.5%, less than 0.4%, less than 0.3%, less than 0.2%, less than 0.1% w/w, and no 0.0% w/w of a traditional surfactant. As such this is meant an anionic, cationic, non-ionic and zwiterionic surfactant.

Traditional anionic surfactants include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), docusate (dioctyl sodium sulfosuccinate), perfluorooctanesulfonate (PFOS), alkyl-aryl ether phosphates and alkyl ether phosphates. Traditional cationic surfactants include cetrimonium bromide (CTAB), cetylpyridinium chloride (CPC), and benzalkonium chloride (BAC). Traditional zwiterionic surfactants include cocamidopropyl hydroxysultaine, and cocamidopropyl betaine. Traditional non-ionic surfactants include polyethylene glycol alkyl ethers (such as Brij); polypropylene glycol alkyl ethers; glucoside alkyl ethers, such as decyl glucoside, lauryl glucoside, and octyl glucoside; polyethylene glycol octylphenyl ethers, such as Triton X-100; polyethylene glycol alkylphenyl ethers, such as Nonoxynol-9; Glycerol alkyl esters, such as glyceryl laurate; polyoxyethylene glycol sorbitan alkyl esters, such as the polysorbates; the sorbitan alkyl esters, such as the spams; and the block copolymers of polyethylene glycol and polypropylene glycol, e.g. the poloxamers.

Methods of Treatment

Another embodiment of the disclosure is a method for moisturizing, and protecting, repairing, or restoring the skin lipid barrier of a mammal, the method comprising applying to the skin of the mammal in need thereof an effective amount of a topical oil-in-water emulsion composition comprising:

(a) a discontinuous oil phase;

(b) a continuous aqueous phase comprising water;

(c) a thickening agent;

(d) at least one lamellar membrane structure comprising
(i) an alkyl amphiphilic component, (ii) an ester of a branched fatty acid and a branched fatty alcohol, (iii) a fatty acid, and (iv) a fatty alcohol; and wherein in use the composition has a water vapor transmission rate of less than 65 $g \cdot m^{-2} \cdot hr^{-1}$ measured in vitro using modWVTR test methodology.

A further embodiment of the disclosure is a method for forming an occlusive layer on the skin, the method comprising applying to the skin of a mammal in need thereof an effective amount of a topical oil-in-water emulsion composition comprising:

(a) a discontinuous oil phase;

(b) a continuous aqueous phase comprising water;

(c) a thickening agent;

(d) at least one lamellar membrane structure comprising
(i) an alkyl amphiphilic component, (ii) an ester of a branched fatty acid and a branched fatty alcohol, (iii) a fatty acid, and (iv) a fatty alcohol; and wherein in use the composition has a water vapor transmission rate of less than 65 g·m$^{-2}$·hr$^{-1}$ measured in vitro using modWVTR test methodology The protection and repair of the skin lipid barrier by the compositions of the present invention improves the skin barrier function and conveys numerous additional therapeutic effects to a mammal to which the compositions are applied.

In one embodiment of the disclosure, the compositions described herein provide moisturization to the skin.

The compositions of the invention are applied to the skin at a frequency consistent with the condition of the skin. For example, where the skin is irritated and in need of repair, more frequent application may be required. Alternatively, where the skin is not irritated and the composition is being applied to merely protect the barrier function of the skin, less frequent application may be possible.

Definitions

The term "applying" as used herein refers to any method which, in sound medical or cosmetic practice, delivers the topical composition to the skin of a subject in such a manner so as to provide a positive effect on a dermatological disorder, condition, or appearance.

As used herein, the phrases an "effective amount" or a "therapeutically effective amount" refers to an amount of a composition or component thereof sufficient enough to have a positive effect on the area of application. Accordingly, these amounts are sufficient to modify the skin disorder, condition, or appearance to be treated but low enough to avoid serious side effects, within the scope of sound medical advice. A therapeutically effective amount will cause a substantial relief of symptoms when applied repeatedly over time. Effective amounts will vary with the particular condition or conditions being treated, the severity of the condition, the duration of the treatment, and the specific components of the composition being used.

The term "about" means within an acceptable range for the particular parameter specified as determined by one of ordinary skill in the art, which will depend, in part, on how the value is measured or determined, i.e. the limitations of the measurement system. For example, "about" can mean a range of up to 10% of a given value.

As used herein, the phrase "salts thereof" refers to salts that are pharmaceutically acceptable. Such salts include: (1) acid addition salts, formed with acids such as, for example, acetic acid, benzoic acid, citric acid, gluconic acid, glutamic acid, glutaric acid, glycolic acid, hydrochloric acid, lactic acid, maleic acid, malic acid, malonic acid, mandelic acid, phosphoric acid, propionic acid, sorbic acid, succinic acid, sulfuric acid, tartaric acid, naturally and synthetically derived amino acids, and mixtures thereof; or (2) salts formed when an acidic proton present in the parent compound is either (i) replaced by a metal ion e.g. an alkali metal ion, an alkaline earth metal ion, or an aluminium ion; or (ii) protonates an organic base such as, for example, ethanolamine, diethanolamine, triethanolamine, tromethamine and N-methylglucamine.

"%" as used herein, refers to the percentage by weight. All percentages are based on the percent by weight of the final composition prepared unless otherwise indicated and all totals equal 100% by weight.

As used herein, moles, is a measure of the amount of a chemical species based upon its molecular weight. No. of moles=Mass/Molar Mass Mole % (mol %) is simply the number of moles of a given lamellar forming component used in a formulation relative to the total number of moles of all stated lamellar forming species, expressed as a percentage.

The term "wt/wt" or "by weight", unless otherwise indicated, means the weight of a given component or specified combination of components to the total weight of the composition expressed as a percentage.

As used herein, the term "phytosterol" refers to plant sterols and plant stanols. Plant sterols are naturally occurring cholesterol-like molecules found in all plants, with the highest concentrations occurring in vegetable oils. Plant stanols are hydrogenation compounds of the respective plant sterols. Phytosterols are natural components of common vegetable oils.

It should be understood that the terms "a" and "an" as used herein refer to "one or more" or "at least one" of the enumerated components. It will be clear to one of ordinary skill in the art that the use of the singular includes the plural unless specifically stated otherwise.

The term "and/or" as used herein covers both additively and also alternatively the individual elements of a list which are thus linked so that these elements are to be understood as linked selectively with "and" or respectively with "or". Furthermore, the terms used in the singular of course also comprise the plural.

Throughout the application, descriptions of various embodiments use "comprising" language, however in some specific instances, an embodiment can alternatively be described using the language "consisting essentially of" or "consisting of".

"Substantially free" of a specified component refers to a composition with less than about 1% by weight of the specified component. "Free" of a specified component refers to a composition where the specified component is absent.

As used herein, "mammal" includes, but is not limited to, humans, including pediatric, adult and geriatric patients.

The following examples are illustrative of the present invention and are not intended to be limitations thereon.

Other terms as used herein are meant to be defined by their well-known meanings in the art.

EXAMPLES

Example 1—Evaluation of the Water Vapor Transmission Rate (WVTR) of Compositions Containing DuraQuench IQ and Comparison with Inventive Compositions Containing DuraQuench IQ and Increased Levels of Fatty Alcohol The following oil-in-water cream compositions (Formulations 1-7) were prepared:

TABLE 1

| Ingredients | 1 | 2 | 3 | 4 | 5 | 6 | 7 |
| --- | --- | --- | --- | --- | --- | --- | --- |
| Caprylic/capric triglyceride | 5.0 | 5.0 | 5.0 | 5.0 | 5.0 | 5.0 | 5.0 |
| Diacaprylyl carbonate | 2.5 | 2.5 | 2.5 | 2.5 | 2.5 | 2.5 | 2.5 |

TABLE 1-continued

| Ingredients | 1 | 2 | 3 | 4 | 5 | 6 | 7 |
|---|---|---|---|---|---|---|---|
| Phosphatidylcholine 70%/ lysophosphatidyl choline 6% | 0.0 | 0.0 | 0.0 | 1.25 | 1.25 | 1.25 | 1.25 |
| Behenyl alcohol | 0.0 | 2.5 | 0.0 | 0.0 | 2.5 | 0.0 | 2.5 |
| DuraQuench IQ: Potassium dicetyl phosphate/potassium monocetyl phosphate Isostearyl isostearate Behenic acid Cetyl alcohol | 4.0 | 4.0 | 4.0 | 0.0 | 0.0 | 4.0 | 4.0 |
| Cetearyl alcohol | 0.0 | 0.0 | 2.5 | 0.0 | 0.0 | 0.0 | 0.0 |
| Polyacrylate crosspolymer-6 | 0.50 | 0.50 | 0.50 | 0.50 | 0.50 | 0.50 | 0.50 |
| Hydroxyethyl acrylate/ Sodium acryloyldimethyl taurate copolymer | 0.20 | 0.20 | 0.20 | 0.20 | 0.20 | 0.20 | 0.20 |
| Glycerin | 10.0 | 10.0 | 10.0 | 10.0 | 10.0 | 10.0 | 10.0 |
| Hydroxyacetophenone | 0.50 | 0.50 | 0.50 | 0.50 | 0.50 | 0.50 | 0.50 |
| Pentylene glycol | 5.0 | 5.0 | 5.0 | 5.0 | 5.0 | 5.0 | 5.0 |
| Sodium hyaluronate | 0.10 | 0.10 | 0.10 | 0.10 | 0.10 | 0.10 | 0.10 |
| Niacinamide | 3.0 | 3.0 | 3.0 | 3.0 | 3.0 | 3.0 | 3.0 |
| D-Panthenol | 1.4 | 1.4 | 1.4 | 1.4 | 1.4 | 1.4 | 1.4 |
| Trisodium ethylenediamine disuccinate | 0.10 | 0.10 | 0.10 | 0.10 | 0.10 | 0.10 | 0.10 |
| Water | 67.7 | 65.2 | 65.2 | 70.45 | 67.95 | 66.45 | 63.95 |
|  | 100.0 | 100.0 | 100.0 | 100.0 | 100.0 | 100.0 | 100.0 |

Method of Preparation

The formulations were prepared using the following method:

1. Oil phase ingredients, including the DuraQuench IQ blend were combined, mixed and heated to 85° C.
2. Aqueous phase ingredients were combined, mixed and heated to 75° C.
3. The polymers were added to the oil phase and briefly agitated/mixed.
4. The water phase was added to the oil phase, while mixing between 10-13,000 rpm until the temperature dropped to 60° C. (without external cooling).
5. When the temperature reached 60° C., cooling was accelerated by using a cold water bath (using freshly drawn water). The temperature was reduced to 40° C.
6. Mixing continued until the temperature of the emulsion was reduced to 30° C. The pH of the emulsion was adjusted to about 5.5, with 10% sodium hydroxide (aq.) and water was added to compensate for evaporative loss. The mixture was briefly mixed to incorporate the added water.
7. The final formulation was an oil-in-water cream.

Measurement of Water Vapor Transmission Rate (WVTR)

The ability of the formulations to form an occlusive layer on the skin was evaluated by measuring the water vapor transmission rate (WVTR). The following method, based upon Pennick et al., Intl J Cosmetic Sci, 2012, 34, p 567-574, with minor changes as noted below was used. This method is referenced herein (and in the claims) as mod-WVTR. Notably, this paper also describes a suitable means for testing Lamellar Thickness.

1. Vitro-Skin (IMS Inc., Portland, Me.) was cut into circular discs using a hole-punch. The discs were weighed on an analytical balance. (not Vitro-Corneum as in the Pennick et al. paper.)
2. The discs were taped on opposing edges, rough side up, with adhesive tape and fixed to the glass surface of a pneumatic drive (Byko Drive). A weighted bar was placed on the drive arm and a 50 µm gauge block placed in front of the weighted bar.
3. The test cream was applied in front of the gauge block, such that when the pneumatic arm is actuated a thin film of cream is applied to the surface including the taped Vitro-Skin disc. Typically 4 discs were coated in a single pass of the arm. The button was depressed and the first coat of the disc occurred. The coated discs were left for 8-10 minutes.
4. The adhesive tape was carefully removed and the discs placed onto a mesh drying tray at room temperature. The surface of the drive unit was cleaned and then the process (steps 1-3) repeated for the next system of interest.
5. Once all the systems had received their initial coat of cream, the first (and most dry system) was secured in place for a second application of cream perpendicular to the first cream coat. The discs were then removed and allowed to partially dry for 60 minutes. The process was repeated for the other creams.
6. The coated discs were reweighed and the weight of applied cream determined.
7. Following partial drying, the WVTR cells were filled with 190 µL of deionized water. The discs were then secured in place over the water, coated side up, using the upper portion of the WVTR cell which was screwed into place. The loaded cells were then reweighed to give the initial weight. The WVTR cells are commercially available from Payne Cells from SMS (Surface Measurement Systems, UK).
8. The WVTR cells were placed in a desiccator over silica gel desiccant. Relative humidity was typically 24-28% RH. The cells were removed periodically.
9. Weight values were determined over the 45-240 minute period. WVTR was calculated using the standard WVTR formula described by Pennick et al (International Journal of Cosmetic Science, vol. 34, pp 567-574, 2012). Non-normalized WVTR values were obtained.

The WVTR was calculated by the formula:

$$WVTR (g.m^{-2}.hr^{-1}) = \frac{\text{Water Loss (g) } (W_{0.75} - W_{3.0})}{\text{Area of Membrane (m}^2\text{)} \times \text{Time (h)}} \quad \text{Formula 1}$$

The area of the membrane was $1.22 \times 10^{-4}$ m$^2$. $W_{0.75}$ and $W_{3.0}$ were the WVTR cell weights in grams at the 0.75 and 3 hour time points respectively.

The water vapor transmission rates obtained from the experiment are illustrated in Table 2:

TABLE 2

| Formula | Composition | WVTR g·m$^{-2}$·hr$^{-1}$ | Std Dev | Lamellar thickness (Å) |
|---|---|---|---|---|
| 1 | Cream + 4% DuraQuench IQ | 93.1 | 7.51 | 53 |
| 2 | Cream + 4% DuraQuench IQ + 2.5% behenyl alcohol | 57.7 | 2.78 | 150 |
| 3 | Cream + DuraQuench IQ + 2.5% cetearyl alcohol | 62.4 | 2.23 | 120 |
| 4 | Cream + 1.25% phosphatidylcholine | 89.3 | 5.34 | 62 |
| 5 | Cream + 2.5% behenyl alcohol + 1.25% phosphatidylcholine | 90.5 | 3.44 | 84, 74, 60, 44 |
| 6 | Cream + 4% DuraQuench IQ + 1.25% phosphatidylcholine | 78.0 | 1.79 | 06 |
| 7 | Cream + 4% DuraQuench IQ + 2.5% behenyl alcohol + 1.25% phosphatidylcholine | 61.8 | 3.22 | 116 |

The data illustrates that the cream composition containing the commercially available DuraQuench IQ blend (Formulation 1) had a WVTR of 93.1 g·m$^{-2}$·hr$^{-1}$. The addition of 2.5% behenyl alcohol resulted in a dramatic reduction in the WVTR to 57.7 g·m$^{-2}$·hr$^{-1}$, which is consistent with the formation of an occlusive layer (see Formulation 2). The addition of the behenyl alcohol also increased the lamellar thickness, and increased the critical packing parameter (CPP) to about 1 which is consistent with the formation of lamellar membranes. A similar result was observed when 2.5% cetearyl alcohol was used in place of 2.5% behenyl alcohol (Formulation 3).

Simply adding a phospholipid (1.25% phosphatidylcholine) to the cream composition did not provide a composition capable of forming an occlusive layer on the skin (Formulation 4). The addition of 2.5% behenyl alcohol to the phospholipid did not materially change the WVTR (Formulation 5).

The addition of the DuraQuench IQ blend and 1.25% phosphatidylcholine reduced the WVTR (Formulation 6), but not to the same extent of the composition comprising the DuraQuench IQ blend and either behenyl alcohol or cetearyl alcohol (Formulations 2 and 3, respectively). The composition comprising the DuraQuench IQ blend, 2.5% behenyl alcohol and 1.25% phosphatidylcholine also demonstrated a large reduction in the WVTR, consistent with the formation of an occlusive layer on the skin (Formulation 7).

Taken together, the data illustrates that the addition of a second fatty alcohol, such as cetearyl alcohol or behenyl alcohol, to a composition containing the DuraQuench IQ blend (which already contains cetyl alcohol) materially reduces the WVTR. This is consistent with the formation of an occlusive layer on the skin in use.

Example 2—Design of Experiments (DOE)

Since Formulation 7 was observed to display good occlusivity, the effect of varying the levels of DuraQuench IQ (2-6%), behenyl alcohol (1-4%) and phosphatidylcholine (0.5-2%) was studied.

The following compositions (Formulations 8-18 shown in Tables 3-5) were prepared using the same method as described in Example 1:

TABLE 3

| Ingredients | 8 | 9 | 10 | 11 |
|---|---|---|---|---|
| Caprylic/capric triglyceride | 5.0 | 5.0 | 5.0 | 5.0 |
| Diacaprylyl carbonate | 2.5 | 2.5 | 2.5 | 2.5 |
| Phosphatidyl choline 70% + lysophosphatidyl choline 6% | 0.5 | 0.5 | 1.25 | 0.5 |
| Behenyl alcohol | 1.0 | 4.0 | 2.5 | 1.0 |
| DuraQuench IQ: Potassium dicetyl phosphate/ Potassium monocetyl phosphate Isostearyl isostearate Behenic acid Cetyl alcohol | 6.0 | 2.0 | 4.0 | 2.0 |
| Polyacrylate crosspolymer-6 | 0.50 | 0.50 | 0.50 | 0.50 |
| Hydroxyethyl acrylate/ sodium acryloyldimethyl taurate copolymer | 0.20 | 0.20 | 0.20 | 0.20 |
| Glycerin | 10.0 | 10.0 | 10.0 | 10.0 |
| Hydroxyacetophenone | 0.50 | 0.50 | 0.50 | 0.50 |
| Pentylene glycol | 5.0 | 5.0 | 5.0 | 5.0 |
| Sodium hyaluronate | 0.10 | 0.10 | 0.10 | 0.10 |
| Niacinamide | 3.0 | 3.0 | 3.0 | 3.0 |
| D-Panthenol | 1.4 | 1.4 | 1.4 | 1.4 |
| Trisodium ethylenediamine disuccinate | 0.10 | 0.10 | 0.10 | 0.10 |
| Water | 64.2 | 65.2 | 63.95 | 68.2 |
| | 100.0 | 100.0 | 100.0 | 100.0 |

TABLE 4

| Ingredients | 12 | 13 | 14 | 15 |
|---|---|---|---|---|
| Caprylic/capric triglyceride | 5.0 | 5.0 | 5.0 | 5.0 |
| Diacaprylyl carbonate | 2.5 | 2.5 | 2.5 | 2.5 |
| Phosphatidyl choline 70%/ lysophosphatidyl choline 6% | 1.25 | 1.25 | 2.0 | 2.0 |
| Behenyl alcohol | 2.5 | 2.5 | 4.0 | 4.0 |
| DuraQuench IQ: Potassium dicetyl phosphate/ Potassium monocetyl phosphate Isostearyl isostearate Behenic acid Cetyl alcohol | 4.0 | 4.0 | 2.0 | 6.0 |
| Polyacrylate crosspolymer-6 | 0.50 | 0.50 | 0.50 | 0.50 |
| Hydroxyethyl acrylate/ sodium acryloyldimethyl taurate copolymer | 0.20 | 0.20 | 0.20 | 0.20 |
| Glycerin | 10.0 | 10.0 | 10.0 | 10.0 |
| Hydroxyacetophenone | 0.50 | 0.50 | 0.50 | 0.50 |
| Pentylene glycol | 5.0 | 5.0 | 5.0 | 5.0 |
| Sodium hyaluronate | 0.10 | 0.10 | 0.10 | 0.10 |
| Niacinamide | 3.0 | 3.0 | 3.0 | 3.0 |
| D-Panthenol | 1.4 | 1.4 | 1.4 | 1.4 |
| Trisodium ethylenediamine disuccinate | 0.10 | 0.10 | 0.10 | 0.10 |
| Water | 63.95 | 63.95 | 63.7 | 59.7 |
| | 100.0 | 100.0 | 100.0 | 100.0 |

TABLE 5

| Ingredients | 16 | 17 | 18 |
|---|---|---|---|
| Caprylic/capric triglyceride | 5.0 | 5.0 | 5.0 |
| Diacaprylyl carbonate | 2.5 | 2.5 | 2.5 |
| Phosphatidyl choline 70%/ lysophosphatidyl choline 6% | 2.0 | 0.5 | 2.0 |
| Behenyl alcohol | 1.0 | 4.0 | 1.0 |
| DuraQuench IQ: Potassium dicetyl phosphate/ Potassium monocetyl phosphate Isostearyl isostearate Behenic acid Cetyl alcohol | 2.0 | 6.0 | 6.0 |

TABLE 5-continued

| Ingredients | 16 | 17 | 18 |
|---|---|---|---|
| Polyacrylate crosspolymer-6 | 0.50 | 0.50 | 0.50 |
| Hydroxyethyl acrylate/ sodium acryloyldimethyl taurate copolymer | 0.20 | 0.20 | 0.20 |
| Glycerin | 10.0 | 10.0 | 10.0 |
| Hydroxyacetophenone | 0.50 | 0.50 | 0.50 |
| Pentylene glycol | 5.0 | 5.0 | 5.0 |
| Sodium hyaluronate | 0.10 | 0.10 | 0.10 |
| Niacinamide | 3.0 | 3.0 | 3.0 |
| D-Panthenol | 1.4 | 1.4 | 1.4 |
| Trisodium ethylenediamine disuccinate | 0.10 | 0.10 | 0.10 |
| Water | 66.7 | 61.2 | 62.7 |
| | 100.0 | 100.0 | 100.0 |

The water vapor transmission rate (WVTR) for each composition was determined using the method described in Example 1. See Table 6:

TABLE 6

| Formula | DuraQuench % w/w | Behenyl alcohol % w/w | Phospholipid % w/w | WVTR g·m$^{-2}$·hr$^{-1}$ | Std Dev |
|---|---|---|---|---|---|
| 8 | 6 | 1 | 0.5 | 57.2 | 2.02 |
| 9 | 2 | 4 | 0.5 | 55.1 | 1.33 |
| 10 | 4 | 2.5 | 1.25 | 56.9 | 2.39 |
| 11 | 2 | 1 | 0.5 | 70.8 | 1.38 |
| 12 | 4 | 2.5 | 1.25 | 60.6 | 3.08 |
| 13 | 4 | 2.5 | 1.25 | 57.2 | 1.7 |
| 14 | 2 | 4 | 2 | 65.6 | 2.75 |
| 15 | 6 | 4 | 2 | 57.5 | 2.11 |
| 16 | 2 | 1 | 2 | 82.9 | 4.01 |
| 17 | 6 | 4 | 0.5 | 50.8 | 1.09 |
| 18 | 6 | 1 | 2 | 71.7 | 3.47 |

Figure 2:
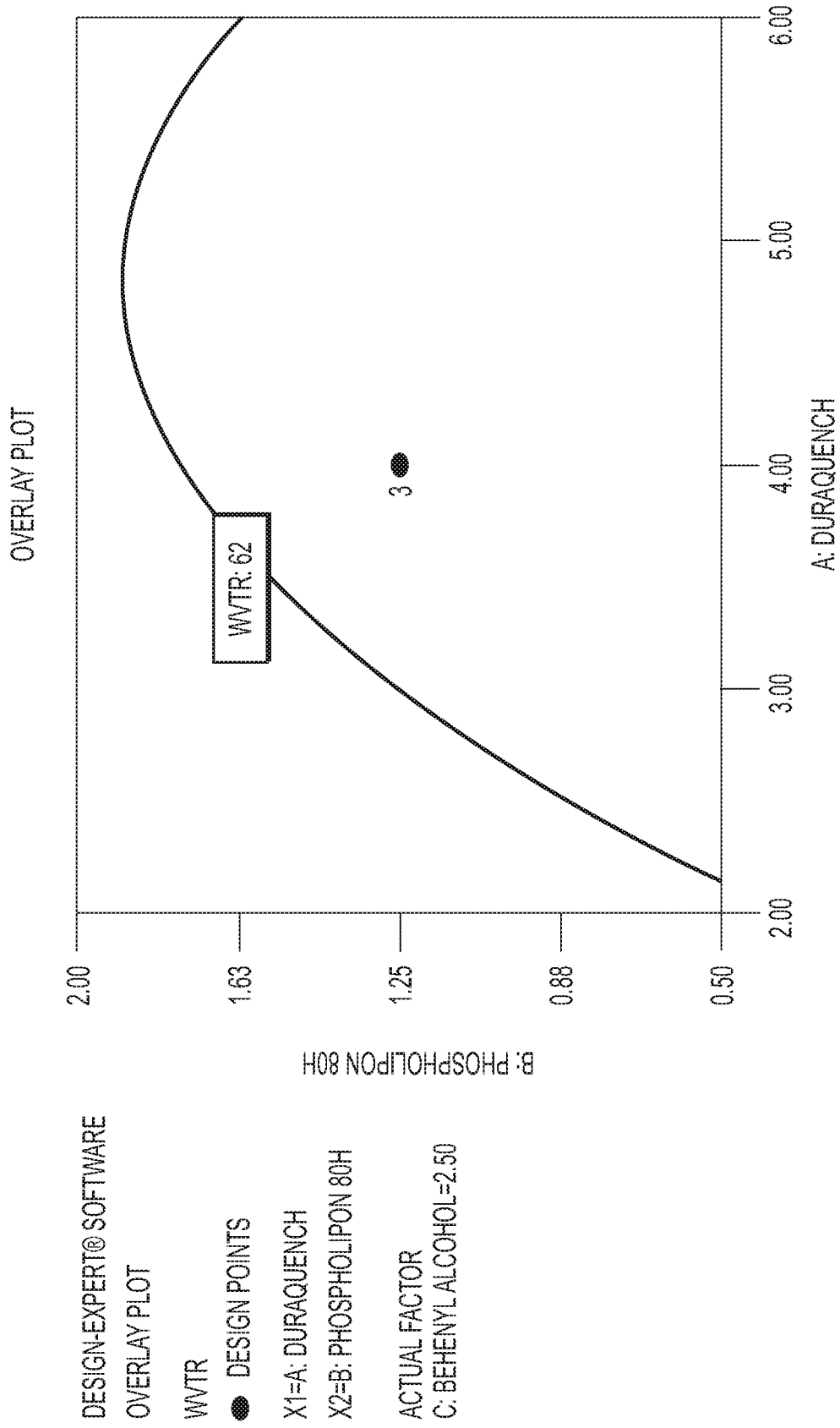
FIG. 2 illustrates the desirable region (light gray) where the WVTR is less than 62 $g \cdot m^{-2} \cdot hr^{-1}$ for compositions containing 2.5% behenyl alcohol with varying levels of DuraQuench IQ and phospolipid.

FIG. 1 illustrates the desirable region (light gray) where the WVTR is less than 62 g·m$^{-2}$·hr$^{-1}$ for compositions containing 1% behenyl alcohol with varying levels of DuraQuench IQ and phospolipid. Where 1% behenyl alcohol is used, there is only a limited region where the WVTR is less than 62 g·m$^{-2}$·hr$^{-1}$. In contrast, where 2.5% behenyl alcohol is used, an expanded desirable region (light gray) may be observed—i.e. where the WVTR is less than 62 g·m$^{-2}$·hr$^{-1}$. See FIG. 2. The data suggests that higher levels of behenyl alcohol (i.e. >1% such as 2.5% or 4%) are preferred, which was confirmed by experiments with 4% behenyl alcohol where the WVTR was less than 62 g·m$^{-2}$·hr$^{-1}$, provided the level of DuraQuench IQ was greater than 2%.

Example 3—Evaluation of the Role of the Dialkyl Phosphate Component in DuraQuench IQ To evaluate the role of the dialkyl amphiphilic component in the DuraQuench IQ blend, the potassium dicetyl phosphate was replaced with potassium monocetyl phosphate. In addition, the cetyl alcohol in DuraQuench IQ was replaced with cetearyl alcohol. The following formulations were prepared using the same method described in Example 1:

TABLE 7

| Ingredients | 19 | 20 | 21 | 22 | 23 |
|---|---|---|---|---|---|
| Caprylic/capric triglyceride | 5.0 | 5.0 | 5.0 | 5.0 | 5.0 |
| Diacaprylyl carbonate | 2.5 | 2.5 | 2.5 | 2.5 | 2.5 |
| Phosphatidyl choline 70%/lysophosphatidyl choline 6% | 0.0 | 2.5 | 1.25 | 1.25 | 1.25 |
| Behenyl alcohol | 2.5 | 2.5 | 0.0 | 2.5 | 2.5 |
| Cetearyl alcohol | 1.48 | 1.48 | 1.48 | 0.0 | 1.48 |
| Isostearyl isostearate | 0.9 | 0.9 | 0.9 | 0.9 | 0.9 |
| Potassium monocetyl phosphate | 0.4 | 0.4 | 0.4 | 0.4 | 0.4 |
| Behenic acid | 0.9 | 0.9 | 0.9 | 0.9 | 0.0 |
| Polyacrylate crosspolymer-6 | 0.88 | 0.50 | 0.88 | 0.88 | 0.88 |
| Hydroxyethyl acrylate/ sodium acryloyldimethyl taurate copolymer | 0.35 | 0.20 | 0.35 | 0.35 | 0.35 |
| Glycerin | 10.0 | 10.0 | 10.0 | 10.0 | 10.0 |
| Hydroxyacetophenone | 0.50 | 0.50 | 0.50 | 0.50 | 0.50 |
| Pentylene glycol | 5.0 | 5.0 | 5.0 | 5.0 | 5.0 |
| Sodium hyaluronate | 0.10 | 0.10 | 0.10 | 0.10 | 0.10 |
| Niacinamide | 3.0 | 3.0 | 3.0 | 3.0 | 3.0 |
| D-Panthenol | 1.4 | 1.4 | 1.4 | 1.4 | 1.4 |
| Trisodium ethylenediamine disuccinate | 0.10 | 0.10 | 0.10 | 0.10 | 0.10 |
| Water | 64.99 | 63.02 | 66.24 | 65.22 | 64.64 |
| | 100.0 | 100.0 | 100.0 | 100.0 | 100.0 |

TABLE 8

| Ingredients | 24 | 25 | 26 | 27 | 28 |
|---|---|---|---|---|---|
| Caprylic/capric triglyceride | 5.0 | 5.0 | 5.0 | 5.0 | 5.0 |
| Diacaprylyl carbonate | 2.5 | 2.5 | 2.5 | 2.5 | 2.5 |
| Phosphatidyl choline 70%/lysophosphatidyl choline 6% | 1.25 | 1.25 | 1.25 | 1.25 | 1.25 |
| Behenyl alcohol | 2.5 | 2.5 | 2.5 | 2.5 | 2.5 |
| Cetearyl alcohol | 1.48 | 1.48 | 1.48 | 1.48 | 1.48 |
| Isostearyl isostearate | 0.0 | 0.9 | 1.8 | 1.8 | 1.8 |
| Potassium monocetyl phosphate | 0.4 | 0.0 | 0.4 | 0.8 | 1.2 |
| Behenic acid | 0.9 | 0.9 | 1.8 | 1.8 | 1.8 |
| Polyacrylate crosspolymer-6 | 0.88 | 0.50 | 0.50 | 0.50 | 0.50 |
| Hydroxyethyl acrylate/ sodium acryloyldimethyl taurate copolymer | 0.35 | 0.20 | 0.20 | 0.20 | 0.20 |
| Glycerin | 10.0 | 10.0 | 10.0 | 10.0 | 10.0 |
| Hydroxyacetophenone | 0.50 | 0.50 | 0.50 | 0.50 | 0.50 |
| Pentylene glycol | 5.0 | 5.0 | 5.0 | 5.0 | 5.0 |
| Sodium hyaluronate | 0.10 | 0.10 | 0.10 | 0.10 | 0.10 |
| Niacinamide | 3.0 | 3.0 | 3.0 | 3.0 | 3.0 |
| D-Panthenol | 1.4 | 1.4 | 1.4 | 1.4 | 1.4 |
| Trisodium ethylenediamine disuccinate | 0.10 | 0.10 | 0.10 | 0.10 | 0.10 |
| Water | 64.64 | 64.67 | 62.47 | 62.07 | 61.67 |
| | 100.0 | 100.0 | 100.0 | 100.0 | 100.0 |

The water vapor transmission rate (WVTR) for each composition was determined using the method described in Example 1. See Table 9:

TABLE 9

| Formula | Composition | WVTR g · m$^{-2}$ · hr$^{-1}$ | Std Dev | Lamellar thickness (A°) | |
|---|---|---|---|---|---|
| 2 | Cream + DuraQuench IQ + 2.5% behenyl alcohol | 57.7 | 2.78 | 150 | |
| 19 | Cream + 0.4% potassium monocetyl phosphate + 0.9% isostearyl isostearate + 0.9% behenic acid + 1.48% cetearyl alcohol + 2.5% behenyl alcohol | 63.4 | 3.23 | 138 | Replaced potassium dicetyl phosphate with potassium monocetyl phosphate and replaced cetyl alcohol with cetearyl alcohol |
| 20 | Cream + 0.4% potassium monocetyl phosphate + 0.9% isostearyl isostearate + 0.9% behenic acid + 1.48% cetearyl alcohol + 2.5% behenyl alcohol + 1.25% phosphatidyl choline | 62.9 | 1.89 | 102 | Add phosphatidyl choline |
| 21 | Cream + 0.4% potassium monocetyl phosphate + 0.9% isostearyl isostearate + 0.9% behenic acid + 1.48% cetearyl alcohol + 1.25% phosphatidyl choline | 73.9 | 3.3 | | Removed behenyl alcohol |
| 22 | Cream + 0.4% potassium monocetyl phosphate + 0.9% isostearyl isostearate + 0.9% behenic acid + 2.5% behenyl alcohol + 1.25% phosphatidyl choline | 82.4 | 2.59 | | Removed cetearyl alcohol |
| 23 | Cream + 0.4% potassium monocetyl phosphate + 0.9% isostearyl isostearate + 1.48% cetearyl alcohol + 2.5% behenyl alcohol + 1.25% phosphatidyl choline | 70.9 | 3.72 | 100 | Removed behenic acid |
| 24 | Cream + 0.4% potassium monocetyl phosphate + 0.9% behenic acid + 1.48% cetearyl alcohol + 2.5% behenyl alcohol + 1.25% phosphatidyl choline | 72.5 | 5.12 | 123 | Removed isostearyl isostearate |
| 25 | Cream + 0.9% isostearyl isostearate + 0.9% behenic acid + 1.48% cetearyl alcohol + 2.5% behenyl alcohol + 1.25% phosphatidyl choline | 69.3 | 0.59 | 107; 100 | Removed potassium monocetyl phosphate |
| 26 | Cream + 0.4% potassium monocetyl phosphate + 1.8% isostearyl isostearate + 1.8% behenic acid + 1.48% cetearyl alcohol + 2.5% behenyl alcohol + 1.25% phosphatidyl choline | 57.7 | 2.91 | | Increase isostearyl isostearate and behenic acid |
| 27 | Cream + 0.8% potassium monocetyl phosphate + 1.8% isostearyl isostearate + 1.8% behenic acid + 1.48% cetearyl alcohol + 2.5% behenyl alcohol + 1.25% phosphatidyl choline | 56.4 | 1.2 | | Increased % potassium monocetyl phosphate |
| 28 | Cream + 1.2% potassium monocetyl phosphate + 1.8% isostearyl isostearate + | 58.6 | 3.72 | | Increased % potassium monocetyl phosphate |

TABLE 9-continued

| Formula Composition | WVTR g·m$^{-2}$·hr$^{-1}$ | Std Dev | Lamellar thickness (A°) |
|---|---|---|---|
| 1.8% behenic acid + 1.48% cetearyl alcohol + 2.5% behenyl alcohol + 1.25% phosphatidyl choline | | | |

The data illustrates that an occlusive effect may also be obtained when the DuraQuench IQ blend is modified by substituting potassium dicetyl phosphate with potassium monocetyl phosphate, and also by substituting cetyl alcohol with cetearyl alcohol, and also adding 2.5% behenyl alcohol (see Formulation 19). A phospholipid such as phosphatidyl choline may optionally be added (see Formulation 20).

Importantly, the data demonstrates that the occlusive effect is lost where either the behenyl alcohol, the cetearyl alcohol, the behenic acid, the isostearyl isostearate or the potassium monocetyl phosphate is removed (see Formulations 21-25, respectively). Collectively, this illustrates the importance of each of the potassium monocetyl phosphate, isostearyl isostearate, behenic acid and combination of cetearyl alcohol and behenyl alcohol to the occlusive effect of the topical composition. That is, the alkyl amphiphilic component, the ester of a branched fatty acid and a branched fatty alcohol, the fatty acid, and fatty alcohol are all important components of the composition, particularly for the formation of an occlusive layer on the skin. Further, the data also illustrates that it is important that the composition contain increased levels of fatty alcohols such as a combination of cetearyl alcohol and behenyl alcohol. This is also consistent with Formulations 2 and 3 which demonstrated the importance of a combination of cetyl alcohol and behenyl alcohol, and cetyl alcohol and cetearyl alcohol, respectively.

The data also illustrated that increasing the level of isostearyl isostearate and behenic acid modestly increased the occlusive effect of the composition (see Formulation 26 and compare with Formulation 20). The data also illustrates that potassium monocetyl phosphate may be used as an alternative to potassium dicetyl phosphate, but beyond a certain point does not necessarily result in a large reduction of WVTR on its own.

Example 4—A Lip Protectant Composition

The following lip protectant composition having the following formulation illustrates the invention:

TABLE 10

| Ingredients | % w/w |
|---|---|
| Lamellar membrane blend: Potassium dicetyl phosphate/potassium monocetyl phosphate, isostearyl isostearate, behenic acid, cetyl alcohol, and behenyl alcohol | 10.00 |
| Trisodium ethylenediamine disuccinate | 0.05 |
| Tocopherol | 0.10 |
| Ascorbyl palmitate | 0.01 |
| Diethylhexyl syringylidene malonate (9.990%) Caprylic/Capric triglyceride (1.110%) | 11.10 |
| Butyl methoxydibenzoylmethane (Avobenzone) | 2.78 |
| *Butyrospermum parkii* | 7.50 |
| Behenyl alcohol | 2.50 |
| VP/Eicosene copolymer | 0.10 |
| Vegetable oil | 7.00 |
| Ethylhexyl salicylate (Octisalate) | 4.55 |
| Sodium carbomer | 0.05 |
| Acrylates/C10-30 alkyl acrylate crosspolymer | 0.05 |
| Water | 18.29 |
| Glycerin | 20.67 |
| Caprylyl glycol | 0.20 |
| Capryloyl glycine | 1.00 |
| Sodium hydroxide (10% w/w) | 1.85 |
| Dehydroxanthan gum | 0.20 |
| Glucose monohydrate | 12.00 |
| Total | 100.00 |

The composition is prepared in two key steps. In the first step, a blend (pastilles) having the lamellar membrane structure* composition is prepared. The pastilles are formed by, for example, combining potassium dicetyl phosphate/potassium monocetyl phosphate, isostearyl isostearate, behenic acid, cetyl alcohol and behenyl alcohol to form a blend. The blend is neutralized with potassium hydroxide, the residual water removed and then the blend pastillated to form pastilles.

In a second step, the blend is added to the composition during the formulation of an oil-in-water emulsion to give the final composition as follows:

Phase 1 (Aqueous):
18.29% by weight Water
0.20% by weight Caprylyl glycol
12.00% by weight Glucose monohydrate
0.20% by weight Dehydroxanthan gum
20.67% by weight Glycerin
1.85% by weight NaOH (10% w/w)
1.00% by weight Capryloyl glycine
Phase 2 (Oil):
7.50% by weight Butyrospermum parkii butter
2.50% by weight Behenyl alcohol
0.10% by weight VP/eicosene copolymer
11.10% by weight Diethylhexyl syringylidene malonate/caprylic/capric triglyceride
2.78% by weight Butyl methoxydibenzoylmethane
0.01% by weight Ascorbyl palmitate
4.55% by weight Ethylhexyl salicylate
Phase 3 (Thickening):
7.00% by weight Olus (vegetable) oil
0.05% by weight Sodium carbomer
0.05% by weight Acrylates/C10-30 alkyl acrylate crosspolymer
Phase 4 (Lamellar membrane structure component):
0.10% by weight Tocopherol
0.05% by weight Trisodium ethylenediamine disuccinate
10.00% by weight Lamellar membrane structure blend Phase 1 and Phase 2 are first heated to 83° C. (+/−3 deg C.) for production. Phase 2 is then slowly added to Phase 1 and the mixture is continuously stirred. The combined Phases are then homogenized for a minimum of 5 minutes at 15,000 RPM with a hand held homogenizer. The combined phases are allowed to cool to 65° C. with continuous stirring. Phase 3 is then added to the combined Phases 1 and 2 and mixed for a minimum of 5 minutes. The combined Phases (1, 2, and 3) are then cooled to 35° C. with continuous stirring in a water bath. Phase 4 is then added to Phases 1, 2, and 3 with continuous stirring. The mixture is then homogenized again for a minimum of 10 minutes at 12,000 RPM. The lip protectant composition is deaerated and allowed to rest overnight.

Example 5—Comparison of Exemplary Formulations

The molar ratios of the Duraquench compositions in comparison to the present invention can be more readily seen by the molar percentages shown below.

Duraquench IQ

| Ingredient | % w/w | molecular wt | moles | mole % |
|---|---|---|---|---|
| ISIS | 22.5 | 536.96 | 0.04 | 14.38 |
| K+ dicetyl phosphate | 18 | 584.94 | 0.03 | 10.56 |
| Behenic Acid | 22.5 | 340.58 | 0.07 | 22.67 |
| Cetyl OH | 37 | 242.44 | 0.15 | 52.38 |
|  |  |  | 0.29 | 100 |

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A topical oil-in-water emulsion composition comprising:
    (a) a discontinuous oil phase;
    (b) a continuous aqueous phase comprising water;
    (c) a thickening agent;
    (d) at least one lamellar membrane structure comprising
        (i) an alkyl amphiphilic component, (ii) an ester of a branched fatty acid and a branched fatty alcohol which is isostearyl isostearate, (iii) a fatty acid which is behenic acid, (iv) a mixture of fatty alcohols comprising at least two selected from the group consisting of cetyl alcohol, cetearyl alcohol and behenyl alcohol, and
        (v) a phospholipid which is hydrogenated phosphatidylcholine;
    wherein the ester and alkyl amphiphilic component are in a weight ratio of about 10:1 to about 1:10; the fatty acid and alkyl amphiphilic component are in a weight ratio of about 10:1 to about 1:10; the fatty alcohol and alkyl amphiphilic component are in a weight ratio of about 20:1 to about 2:1; and the alkyl amphiphilic component and phospholipid are in a molar ratio of about 35:1 to about 6:1; and
    wherein in use the composition has a water vapor transmission rate of less than 65 $g \cdot m^{-2} \cdot hr^{-1}$ measured in vitro using the modWVTR test methodology.

2. The composition according to claim 1, wherein the mixture of fatty alcohols comprises cetyl alcohol and behenyl alcohol, and a molar ratio of behenyl alcohol to cetyl alcohol is from about 4:1 to about 0.35:1.

3. The composition according to claim 1, wherein the alkyl amphiphilic component is a dialkyl amphiphilic component, or a monoalkyl amphiphilic component.

4. The composition according to claim 3, wherein the alkyl amphiphilic component is a dialkyl amphiphilic component and each alkyl group is independently selected from the group consisting of C14 to C22 alkyl groups.

5. The composition according to claim 4, wherein the alkyl groups are each C16 alkyl groups.

6. The composition according to claim 3, wherein the alkyl amphiphilic component is a monoalkyl amphiphilic component and the alkyl group is selected from the group consisting of C14 to C22 alkyl groups.

7. The composition according to claim 6, wherein the alkyl group is a C16 alkyl group.

8. The composition according to claim 1, wherein the alkyl amphiphilic component is potassium dicetyl phosphate or a potassium monocetyl phosphate.

9. The composition according to claim 1 wherein the composition has a mole % of the ester of about 5.0% to about 18%.

10. The composition according to claim 1 comprising a mole % of about 2.0 to about 11 mol % of the alkyl amphiphilic component; about 5.0% to about 18% mol % of the ester; about 6% to about 20 mol % of the fatty acid; and about 50 to about 85 mol % of the alcohol, and about 2.0 to about 8.0 mol % of the phosphatidylcholine.

11. The composition according to claim 1, wherein the composition has a water vapor transmission rate of less than 62 $g \cdot m^{-2} \cdot hr^{-1}$ measured in vitro.

12. A method for moisturizing, and protecting, repairing, or restoring the skin lipid barrier of a mammal, the method comprising applying to the skin of the mammal in need thereof an effective amount of a topical oil-in-water emulsion composition comprising:
    (a) a discontinuous oil phase;
    (b) a continuous aqueous phase comprising water;
    (c) a thickening agent;
    (d) at least one lamellar membrane structure comprising
        (i) an alkyl amphiphilic component, (ii) an ester of a branched fatty acid and a branched fatty alcohol which is isostearyl isostearate, (iii) a fatty acid which is behenic acid, (iv) a mixture of fatty alcohols comprising at least two selected from the group consisting of cetyl alcohol, cetearyl alcohol and behenyl alcohol, and
        (v) a phospholipid which is hydrogenated phosphatidylcholine;
    wherein the ester and alkyl amphiphilic component are in a weight ratio of about 10:1 to about 1:10; the fatty acid and alkyl amphiphilic component are in a weight ratio of about 10:1 to about 1:10; the fatty alcohol and alkyl amphiphilic component are in a weight ratio of about 20:1 to about 2:1; and the alkyl amphiphilic component and phospholipid are in a molar ratio of about 35:1 to about 6:1; and wherein in use the composition has a water vapor transmission rate of less than 65 $g \cdot m^{-2} \cdot hr^{-}$ measured in vitro using the modWVTR test methodology.

* * * * *